(12) United States Patent
Libbey et al.

(10) Patent No.: US 8,290,593 B2
(45) Date of Patent: Oct. 16, 2012

(54) IMPLANTABLE MEDICAL DEVICE INCLUDING A PLURALITY OF LEAD CONNECTION ASSEMBLIES

(75) Inventors: Robert W. Libbey, St. Michael, MN (US); William T. Donofrio, Andover, MN (US); John E. Burnes, Coon Rapids, MN (US); Paul G. Krause, Shoreview, MN (US); Michael K. Berquist, Parker, TX (US); Olivier Blandin, Lausanne (CH); Michael Hudziak, Stillwater, MN (US); William L. Johnson, Vadnais Heights, MN (US); John E. Nicholson, Blaine, MN (US); George Patras, Greenfield, MN (US); Andrew J. Ries, Lino Lakes, MN (US); Jeffrey Swanson, Cambridge, MN (US); Paul Vahle, Lake Elmo, MN (US); Thomas J. Olson, Ham Lake, MN (US); William K. Wenger, St. Paul, MN (US); Michael R. Klardie, Bloomington, MN (US); Samira Tahvildari, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 253 days.

(21) Appl. No.: 12/610,157

(22) Filed: Oct. 30, 2009

(65) Prior Publication Data
US 2010/0137929 A1 Jun. 3, 2010

Related U.S. Application Data

(63) Continuation-in-part of application No. 12/363,375, filed on Jan. 30, 2009, now Pat. No. 8,200,335.

(60) Provisional application No. 61/110,241, filed on Oct. 31, 2008.

(51) Int. Cl.
*A61N 1/375* (2006.01)
(52) U.S. Cl. .......................................... 607/37
(58) Field of Classification Search ............. 607/36–38; 439/909
See application file for complete search history.

(56) References Cited

U.S. PATENT DOCUMENTS

| 5,261,395 A | 11/1993 | Oleen et al. |
| 5,330,507 A | 7/1994 | Schwartz |
| 5,374,279 A | 12/1994 | Duffin, Jr. et al. |
| 5,388,578 A | 2/1995 | Yomtov et al. |
| 5,522,856 A | 6/1996 | Reineman |

(Continued)

OTHER PUBLICATIONS

International Preliminary Report on Patentability from international application No. PCT/2009/062851, dated May 12, 2011, 9 pp.

(Continued)

*Primary Examiner* — Carl H Layno
*Assistant Examiner* — Jessica Sarcione
(74) *Attorney, Agent, or Firm* — Carol F. Barry

(57) ABSTRACT

An implantable medical device (IMD) may include at least two separate lead connection assemblies, each with electrical connectors for connecting implantable leads to the IMD. In some examples, a IMD may include a first therapy module configured to generate a first electrical stimulation therapy and a second therapy module configured to generate a second electrical stimulation therapy for delivery to the patient. The IMD may include a first lead connection assembly including a first electrical connector electrically coupled to the first therapy module and a second lead connection assembly including a second electrical connector electrically coupled to the second therapy module. In some examples, the first and second lead connection assemblies are distributed around the outer perimeter of the IMD housing.

49 Claims, 14 Drawing Sheets

U.S. PATENT DOCUMENTS

| | | | |
|---|---|---|---|
| 5,775,935 | A | 7/1998 | Barna |
| 6,006,135 | A | 12/1999 | Kast et al. |
| 6,134,470 | A | 10/2000 | Hartlaub |
| 6,327,502 | B1 | 12/2001 | Johansson et al. |
| 6,428,368 | B1 | 8/2002 | Hawkins et al. |
| 6,847,845 | B2 | 1/2005 | Belden |
| 7,096,064 | B2 | 8/2006 | Deno et al. |
| 7,515,964 | B1 | 4/2009 | Alexander et al. |
| 7,567,841 | B2 | 7/2009 | Chan |
| 2003/0073348 | A1 | 4/2003 | Ries et al. |
| 2004/0034392 | A1 | 2/2004 | Spadgenske |
| 2004/0116976 | A1 | 6/2004 | Spadgenske |
| 2004/0193228 | A1 | 9/2004 | Gerber |
| 2005/0065570 | A1 | 3/2005 | Stein et al. |
| 2005/0070968 | A1 | 3/2005 | Bergelson et al. |
| 2005/0192639 | A1 | 9/2005 | Bardy et al. |
| 2005/0255719 | A1 | 11/2005 | Heidlein |
| 2006/0004420 | A1 | 1/2006 | Rossing et al. |
| 2006/0079942 | A1 | 4/2006 | Deno et al. |
| 2006/0217771 | A1 | 9/2006 | Soykan et al. |
| 2007/0123947 | A1 | 5/2007 | Wenger et al. |
| 2007/0255323 | A1 | 11/2007 | Werder et al. |
| 2007/0255331 | A1 | 11/2007 | Gillberg et al. |
| 2007/0276443 | A1 | 11/2007 | Shafer et al. |
| 2008/0015659 | A1 | 1/2008 | Zhang et al. |
| 2008/0208290 | A1 | 8/2008 | Phillips et al. |
| 2008/0242976 | A1 | 10/2008 | Robertson et al. |
| 2009/0112282 | A1 | 4/2009 | Kast et al. |
| 2010/0137929 | A1 | 6/2010 | Libbey et al. |

OTHER PUBLICATIONS

International Search Report and Written Opinion from corresponding PCT/US2009/062851 mailed on Mar. 9, 2010 (15 pgs.).

U.S. Appl. No. 61/110,241, filed Oct. 31, 2008, entitled "Implantable Medical Device Lead Connection Assembly", by Donofrio et al.

U.S. Appl. No. 12/363,375, filed Jan. 30, 2009, entitled "Implantable Medical Device Lead Connection Assembly", by Donofrio et al.

Office Action from U.S. Appl. No. 12/363,375, dated Aug. 31, 2011, 14 pp.

Response to Office Action Aug. 31, 2011, from U.S. Appl. No. 12/363,375, filed Nov. 30, 2011, 13 pp.

IMPLANTABLE MEDICAL DEVICE INCLUDING A PLURALITY OF LEAD CONNECTION ASSEMBLIES

This application is a continuation-in-part of U.S. application Ser. No. 12/363,375, filed Jan. 30, 2009 now U.S. Pat. No. 8,200,335. This application claims the benefit of U.S. Provisional Application No. 61/110,241, entitled, "IMPLANTABLE MEDICAL DEVICE LEAD CONNECTION ASSEMBLY," and filed on Oct. 31, 2008, the entire content of which is incorporated herein by reference.

TECHNICAL FIELD

The disclosure relates to medical devices and, in particular, implantable medical devices configured to deliver electrical stimulation to a patient.

BACKGROUND

A wide variety of implantable medical devices that deliver a therapy or monitor a physiologic condition of a patient have been clinically implanted or proposed for clinical implantation in patients. Some implantable medical devices may employ one or more elongated electrical leads and/or sensors. Such implantable medical devices may deliver therapy or monitor the heart, muscle, nerve, brain, stomach or other organs. In some cases, implantable medical devices deliver electrical stimulation therapy and/or monitor physiological signals via one or more electrodes or sensor elements, at least some of which may be included as part of one or more elongated implantable medical leads. Implantable medical leads may be configured to allow electrodes or sensors to be positioned at desired locations for delivery of stimulation or sensing electrical depolarizations. For example, electrodes or sensors may be located at a distal portion of the lead. A proximal portion of the lead may be coupled to an implantable medical device housing, which may contain electronic circuitry such as stimulation generation and/or sensing circuitry. In some cases, electrodes or sensors may be positioned on an IMD housing as an alternative or in addition to electrodes or sensors deployed on one or more leads.

Implantable cardiac devices, such as cardiac pacemakers or implantable cardioverter defibrillators, provide therapeutic electrical stimulation to the heart by delivering electrical therapy signals such as pulses or shocks for pacing, cardioversion or defibrillation pulses via electrodes of one or more implantable leads. In some cases, an implantable cardiac device may sense intrinsic depolarizations of the heart, and control the delivery of therapeutic stimulation to the heart based on the sensing. When an abnormal rhythm of the heart is detected, such as bradycardia, tachycardia or fibrillation, an appropriate electrical therapy (e.g., in the form of pulses) may be delivered to restore the normal rhythm. For example, in some cases, an implantable medical device may deliver pacing, cardioversion or defibrillation signals to the heart of the patient upon detecting ventricular tachycardia, and deliver cardioversion or defibrillation therapy to a patient's heart upon detecting ventricular fibrillation. Some medical device systems that include a neurostimulator in addition to implantable cardiac device have also been proposed.

SUMMARY

In general, the disclosure is directed to lead connection assemblies for implantable medical devices (IMDs). In some examples, a lead connection assembly of an IMD may include at least two different types of electrical connectors that are configured to electrically connect a respective implantable medical lead to one or more therapy modules of the IMD. In some examples, the IMD may include a lead connection assembly including a first electrical connector and a second electrical connector that has at least one of a different electrical contact arrangement, a different lead connection receptacle geometry or a different size than the first electrical connector. In this way, the electrical connectors may be configured to receive different types of leads.

In some examples, the IMD may include a first therapy module that is configured to deliver an electrical stimulation signal to a patient with one or more electrodes of a first lead that is electrically coupled to the first therapy module via the first electrical connector, and a second therapy module that is configured to deliver a second electrical stimulation signal to the patient with one or more electrodes of a second lead that is electrically coupled to the second therapy module via the second electrical connector. The second electrical connector may be incompatible with the first lead, e.g., to help prevent the first lead from being electrically connected to the second therapy module via the second electrical connector. In addition, in some examples, the first electrical connector may be incompatible with the second lead.

In some examples, the first therapy module may be configured to deliver at least one of pacing, cardioversion, or defibrillation therapy to the heart of a patient via the first lead, and the second therapy module may be configured to deliver an electrical stimulation signal to a nonmyocardial tissue site (e.g., a tissue site proximate a nerve and/or an extravascular tissue site) or a nonvascular cardiac tissue site (e.g., a cardiac fat pad) within the patient via the second lead. The mutually incompatible configurations of the second electrical connector and first lead may help prevent the first lead from delivering electrical stimulation generated by the second therapy module to the heart of a patient.

In some examples, a lead connection assembly of an IMD may include two or more electrical connectors that define openings for receiving leads, whereby the openings face different directions. For example, a lead connection assembly may include a first electrical connector that receives a first lead such that the first lead extends from the housing of the IMD in a first direction, and a second electrical connector that receives a second lead such that the second lead extends from the housing in a second direction that is different than the first direction. In some example, the first and second directions may correspond to the different target tissue sites for delivery of the stimulation therapy by the first and second leads, respectively.

In some examples, an IMD may include a plurality of lead connection assemblies, e.g., a first lead connection assembly and a second lead connection assembly, each of which is configured to electrically and mechanically couple one or more leads to therapy modules within the IMD. In some examples, the IMD may include a first lead connection assembly to deliver a first stimulation therapy generated via a first therapy module to a patient via a first lead. The IMD may also include a second lead connection assembly to deliver a second stimulation therapy generated via a second therapy module to the patient via a second lead. In some examples, the IMD may include a first lead connection assembly used to deliver at least one of pacing, cardioversion, or defibrillation therapy generated by a first therapy module to the heart of a patient via a first lead, and second lead connection assembly used to deliver a second stimulation therapy generated by a second therapy module to the patient via a second lead, where the therapy is a different type of therapy than that delivered by the first lead connection assembly. For example, the second therapy module of the IMD may generate and deliver an electrical stimulation signal to a nonmyocardial tissue site (e.g., a tissue site proximate a nerve and/or an extravascular tissue site) or a nonvascular cardiac tissue site (e.g., a cardiac fat pad) within the patient via the second lead connected to the IMD via the second lead connection assembly.

In one example, the disclosure is directed to an implantable medical system comprising a housing, a first therapy module enclosed within the housing and configured to generate at least one of a pacing, cardioversion or defibrillation therapy that is delivered to a heart of a patient, a second therapy module enclosed within the housing and configured to generate electrical stimulation that is delivered to a tissue site within the patient, and a lead connection assembly. The lead connection assembly comprises a first electrical connector electrically coupled to the first therapy module and configured to electrically connect to a first lead that delivers the at least one of the pacing, cardioversion or defibrillation therapy to the heart of the patient and a second electrical connector electrically coupled to the second therapy module and configured to electrically connect to a second lead that delivers the electrical stimulation to the tissue site. The second electrical connector is configured to be at least partially incompatible with the first lead.

In another example, the disclosure is directed to an implantable medical system comprising a housing, means for generating at least one of a pacing, cardioversion, or defibrillation therapy that is delivered to a heart of a patient, wherein the means for generating the at least one of pacing, cardioversion or defibrillation therapy is enclosed within the housing, means for generating electrical stimulation that is delivered to a tissue site within the patient, wherein the means for generating electrical stimulation is enclosed within the housing, and means for receiving leads. The means for receiving leads comprises means for electrically coupling a first lead to the means for generating the at least one of pacing, cardioversion or defibrillation therapy and means for electrically coupling a second lead to the means for generating the electrical stimulation. The means for electrically coupling the second lead to the means for generating electrical stimulation is configured to be at least partially incompatible with the first lead.

In another example, the disclosure is directed to a method comprising delivering at least one of pacing, cardioversion or defibrillation therapy to a heart of a patient with at least one electrode of a first lead that is electrically coupled to a first therapy module of an implantable medical device, wherein the implantable medical device comprises a first electrical connector that electrically connects the first lead to the first therapy module, and delivering electrical stimulation to a tissue site within the patient with at least one electrode of a second lead that is electrically coupled to a second therapy module of the implantable medical device, wherein the implantable medical device comprises a second electrical connector that electrically connects the second lead to the second therapy module, and wherein the second electrical connector is configured to be at least partially incompatible with the first lead.

In another example, the disclosure is directed to an implantable medical system comprising a housing, a first therapy module enclosed within the housing and configured to generate at least one of a pacing, cardioversion or defibrillation therapy that is delivered to a heart of a patient, a second therapy module enclosed within the device housing and configured to generate electrical stimulation that is delivered to a tissue site within the patient, and a lead connection assembly. The lead connection assembly comprises a first electrical connector electrically coupled to the first therapy module and defining a first opening configured to receive a first lead that delivers the at least one of pacing, cardioversion or defibrillation therapy to the heart of the patient, and a second electrical connector electrically coupled to the second therapy module and defining a second opening configured to receive a second lead that delivers the electrical stimulation to the tissue site of the patient, where the first and second openings face different directions.

In another example, the disclosure is directed to a method comprising delivering at least one of pacing, cardioversion or defibrillation therapy to a heart of a patient via a first lead electrically coupled to a first therapy module of an implantable medical device via a first electrical connector of a lead connection assembly, and delivering electrical stimulation to a tissue site within the patient via a second lead electrically coupled to a second therapy module of the implantable medical device via a second electrical connector of the lead connection assembly. The first lead extends from a housing of the implantable medical device in a first direction and the second lead extends from the housing of the implantable medical device in a second direction that is different from the first direction.

In another example, the disclosure is directed to an implantable medical system comprising a housing; means for delivering at least one of a pacing, cardioversion, or defibrillation therapy to a heart of a patient, the means for delivering the at least one of pacing, cardioversion or defibrillation therapy to the heart of the patient enclosed within the housing; means for delivering electrical stimulation to a tissue site within the patient, the means for delivering electrical stimulation to the tissue site enclosed within the housing; and a lead connection assembly. The lead connection assembly comprising means for electrically coupling a first lead that delivers the at least one of pacing, cardioversion or defibrillation therapy to the means for delivering the at least one of pacing, cardioversion or defibrillation therapy, wherein the means for electrically coupling the first lead defines a first opening to receive the first lead; and means for electrically coupling a second lead that delivers the electrical stimulation to the tissue site to the means for delivering the electrical stimulation to the tissue site, wherein the means for electrically coupling the second lead defines a second opening to receive the second lead, wherein the first and second openings face different directions.

In another example, the disclosure is directed to an implantable medical system comprising a housing, a first therapy module enclosed within the housing and configured to generate a first electrical stimulation therapy for delivery to a patient, a second therapy module enclosed within the device housing and configured to generate a second electrical stimulation therapy for delivery to the patient, a first lead connection assembly including a first electrical connector electrically coupled to the first therapy module; and a second lead connection assembly including a second electrical connector electrically coupled to the second therapy module.

In another example, the disclosure is directed to an implantable medical system comprising a housing, means for generating a first electrical stimulation for delivery to a patient, means for generating a second electrical stimulation for delivery the patient separate from that of the means for generating the second electrical stimulation, means for electrically coupling a first implantable lead to the means for generating first electrical stimulation, means for electrically coupling a second implantable lead to the means for generating second electrical stimulation separate from that of the means for electrically coupling the first implantable lead to the means for generating first electrical stimulation, where the means for generating the first electrical stimulation and the second electrical stimulation are enclosed within the housing.

In another example, the disclosure is directed to a method comprising delivering a first electrical stimulation therapy to a patient via a first lead electrically coupled to a first therapy module of an implantable medical device via a first lead connection assembly; and delivering a second electrical stimulation therapy to the patient via a second lead electrically coupled to a second therapy module of an implantable medical device via a second lead connection assembly.

In another example, the disclosure is directed to a computer-readable medium comprising instructions that cause a programmable processor to perform any part of the techniques described herein.

The details of one or more examples are set forth in the accompanying drawings and the description below. Other features, objects, and advantages of the disclosure will be apparent from the description and drawings, and from the claims.

DETAILED DESCRIPTION

Figure 1:
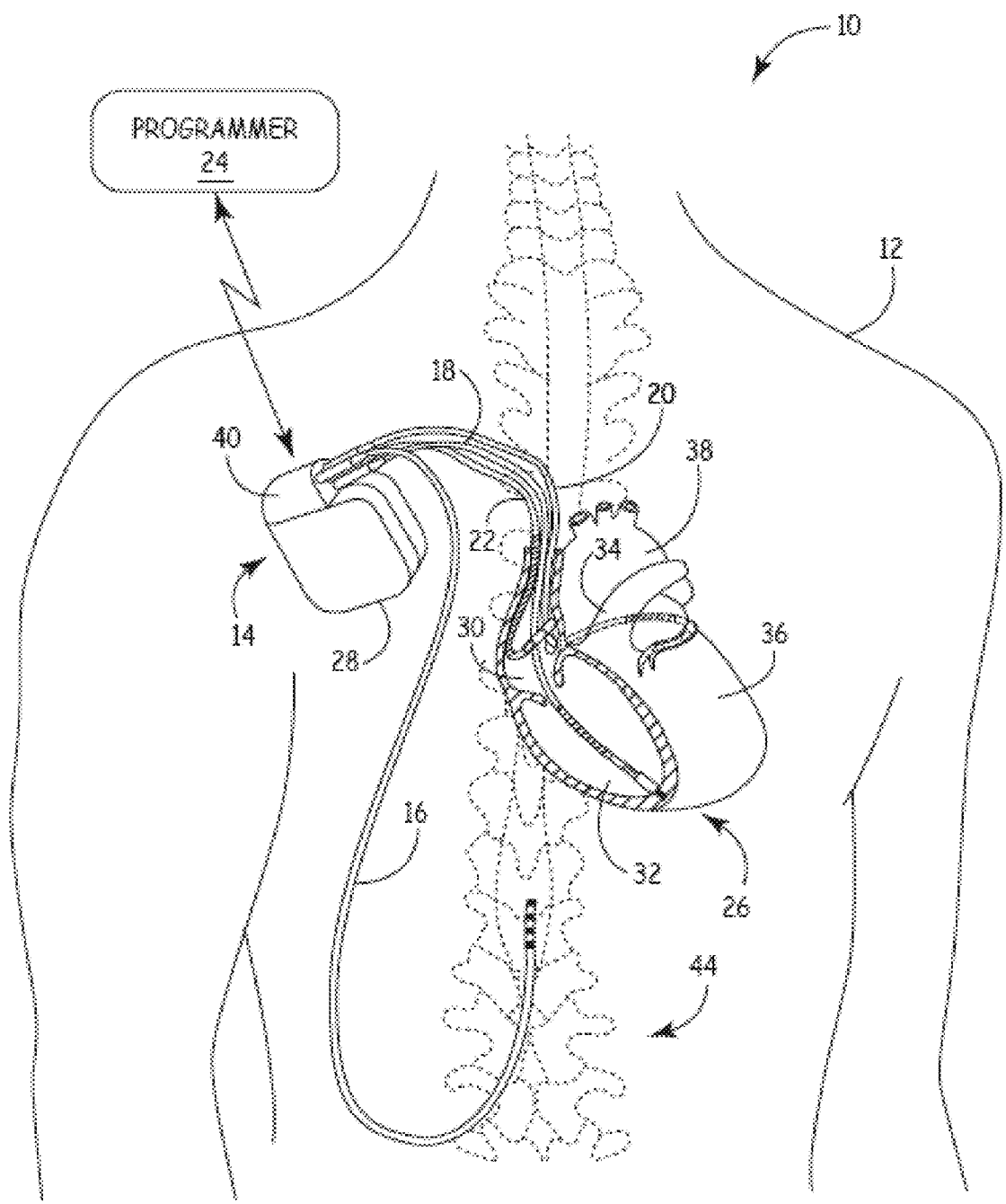
FIG. 1 is a conceptual diagram illustrating an example therapy system that includes an implantable medical device (IMD) configured to deliver electrical stimulation to a tissue site within a patient and deliver cardiac rhythm therapy management to a heart of the patient.

FIG. 1 is a conceptual diagram illustrating an example therapy system 10 that provides therapy to patient 12. Therapy system 10 includes implantable medical device (IMD) 14 and leads 16, 18, 20, 22, and programmer 24. As described in greater detail below, leads 16, 18, 20, 22 are mechanically and electrically coupled to IMD 14 via lead connection assembly 40, which may be connected housing 28 of IMD 14 as shown in FIG. 1. In some examples, housing 28 and lead connection assembly 40 are integrally formed, while in other examples, housing 28 and lead connection assembly 40 are separate components that are mechanically coupled together, e.g., via an adhesive, welding, interlocking components, and the like. In the example shown in FIG. 1, housing 28 and lead connection assembly 40 can be fabricated from any suitable biocompatible material, such as, but not limited to, titanium. Housing 28 and lead connection assembly 40 may be formed from the same material or different materials.

IMD 14 generates and delivers electrical stimulation to heart 26 via electrodes carried by one or more of leads 18, 20, 22 in order to manage a cardiac rhythm of heart 26. Accordingly, IMD 14 includes a first therapy module configured that generates at least one of pacing, cardioversion, or defibrillation therapy. The pacing therapy may include, for example, antitachyarrhythmia pacing (ATP) and pacing therapies designed to prevent ventricular tachycardia, ventricular fibrillation, atrial tachycardia, and/or atrial fibrillation. In some examples, IMD 14 delivers pacing pulses, but not cardioversion or defibrillation pulses, while in other examples, IMD 14 delivers cardioversion or defibrillation pulses, but not pacing pulses. In addition, in further examples, IMD 14 delivers pacing, cardioversion, and defibrillation pulses.

In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 26. Right atrial (RA) lead 22 extends through one or more veins and the vena cava, and into the right atrium 30 of heart 26. In other examples, IMD 14 delivers stimulation therapy to heart 26 by delivering stimulation to an extravascular tissue site in addition to or instead of delivering stimulation via electrodes of intravascular leads 18, 20, 22. An extravascular tissue site is outside of heart 26 and outside of arteries, veins, or other vasculature of patient 12.

IMD 14 may sense electrical signals attendant to the depolarization and repolarization of heart 26 via electrodes (not shown in FIG. 1) coupled to at least one of the leads 18, 20, 22. In some examples, IMD 14 provides pacing pulses to heart 26 based on the electrical signals sensed within heart 26. The configurations of electrodes used by IMD 14 for sensing and pacing may be unipolar or bipolar. IMD 14 may also provide defibrillation therapy and/or cardioversion therapy via electrodes located on at least one of the leads 18, 20, 22. IMD 14 may detect arrhythmia of heart 26, such as fibrillation of ventricles 32 and 36, and IMD 14 may be programmed to deliver a progression of therapies, e.g., pulses with increasing energy levels, until a fibrillation of heart 26 is stopped. IMD 14 may detect fibrillation employing one or more fibrillation detection techniques known in the art.

IMD 14 also comprises a second therapy module that generates electrical stimulation signals that are delivered to a tissue site within patient 12 via lead 16. In some examples, the tissue site may include at least one of a nonmyocardial tissue site or a nonvascular cardiac tissue site. A nonmyocardial tissue site may include a tissue site that does not include cardiac muscle (e.g., the myocardium). For example, a nonmyocardial tissue site may be proximate a muscle other than cardiac muscle, an organ other than the heart, or neural tissue. A tissue site proximate a nerve may be a neural tissue site to which delivery of electrical stimulation may activate the nerve. In some examples, a tissue site proximate a nerve may be in a range of about zero centimeters to about ten centimeters from the nerve, although other distance ranges are contemplated and may depend upon the nerve. The nonmyocardial tissue site may include extravascular tissue sites or intravascular tissue sites. A nonvascular cardiac tissue site may include, for example, a cardiac fat pad.

In some examples, delivery of electrical stimulation to a tissue site proximate a nerve or a nonmyocardial tissue site that may not be proximate a nerve may help modulate an autonomic nervous system of patient 12. In some examples, IMD 14 may deliver electrical stimulation therapy to a nerve of patient 12 via a lead implanted within vasculature (e.g., a blood vessel) of patient 12. In addition, in some examples, IMD 14 may deliver electrical stimulation that is delivered to peripheral nerves that innervate heart 26, or fat pads on heart 26 that may contain nerve bundles. The fat pads may be referred to as a nonvascular cardiac tissue site.

In the example shown in FIG. 1, IMD 14 delivers electrical stimulation to tissue proximate spinal cord 44 of patient 12 via lead 16. In other examples, IMD 14 may be coupled to two or more leads that may, for example, facilitate bilateral spinal cord stimulation of patient 12, although, in some examples, bilateral spinal cord stimulation may also be achieved with a single lead 16 positioned across the patient's midline. Although lead 16 is shown to be introduced into spinal cord 44 near the lumbar region in the example shown in FIG. 1, in other examples, lead 16 may be introduced into spinal cord 44 via the thoracic column. Electrodes of lead 16 may be positioned within an intrathecal space or epidural space of spinal cord 44, or, in some examples, adjacent nerves that branch off of spinal cord 44.

Delivery of electrical stimulation by IMD 14 to one or more target tissues sites, e.g., one or more target tissue sites proximate to a nerve, nerve site, cardiac fat pad, or an extravascular target tissue site that is proximate a nerve, may provide cardioprotective benefits to patient 12. For example, deliver of electrical stimulation to a tissue site proximate a nerve of patient 12 may help treat heart failure. In addition, delivery of electrical stimulation to a nerve of patient 12 to modulate an autonomic nervous system of patient 12 may help reduce or eliminate cardiovascular conditions such as bradycardia, tachycardia, unhealthy cardiac contractions, ischemia, inefficient heart pumping, inefficient collateral circulation of heart 26 or cardiac muscle trauma. In addition, delivery of electrical stimulation by IMD 14 may complement antitachycardia therapy (e.g., antitachycardia pacing, cardioversion or defibrillation) by IMD 14 or provide back-up therapy to the cardiac rhythm therapy provided by the first therapy module.

Stimulation of spinal cord 44 or nerves branching therefrom by IMD 14 may help prevent or mitigate occurrences of tachyarrhythmias and may reduce the level of aggressiveness of the cardiac therapy, such as pacing, cardioversion or defibrillation, delivered by IMD 14. In this way, IMD 14 may operate to help prevent arrhythmias of heart 26 of patient 12, as well as to terminate detected arrhythmias. In other examples, IMD 14 may provide electrical stimulation therapy of a parasympathetic nerve, such as a vagus nerve, of patient 12. Stimulation of a parasympathetic nerve of patient 12 may help slow intrinsic rhythms of heart 26, which may complement antitachyarrhythmia therapy also delivered by IMD 14.

In some examples, depending upon the stimulation target, the delivery of electrical stimulation by IMD 14 via lead 16 may also mitigate perceptible discomfort generated from the delivery of pacing pulses or cardioversion/defibrillation shocks by IMD 14. For example, if IMD 14 delivers electrical stimulation to spinal cord 44 of patient 12, the neurostimulation may produce paresthesia, which may help reduce the discomfort felt by patient 12 from the delivery of pacing pulses or cardioversion/defibrillation shocks by IMD 14.

In other examples, electrodes of lead 16 may be positioned to deliver electrical stimulation to any other suitable nerve, organ, muscle or muscle group in patient 12, which may be selected based on, for example, a therapy program or regimen selected for a particular patient. In some examples, IMD 14 may deliver electrical stimulation to other sympathetic or parasympathetic nerves, baroreceptors, cardiac fat pads, or the carotid sinus or a cardiac branch of the vagal trunk of patient 12 in order to facilitate the delivery of cardiac rhythm therapy by IMD 14, as previously described.

In some examples, IMD 14 may also be referred to as a signal generator, stimulation generator or an electrical stimulator. In some examples, lead 16 may also carry one or more sense electrodes to permit IMD 14 to sense electrical signals within patient 12. In the example of FIG. 1, IMD 14 has been implanted in patient 12 at a location that allows leads 18, 20, 22 to be positioned within heart 26, and allows lead 16 to be positioned proximate spinal cord 44. For example, IMD 14 may be subcutaneously or submuscularly implanted in the body of a patient 12 (e.g., in a chest cavity, lower back, lower abdomen, or buttocks of patient 12).

In the example shown in FIG. 1, a single IMD 14 provides both cardiac rhythm therapy and electrical stimulation therapy other than cardiac rhythm therapy. Accordingly, the components for generating and delivering the pacing, cardioversion and/or defibrillation therapy via leads 18, 20, and 22, and generating and delivering the electrical stimulation therapy to a target tissue site via lead 16 may be substantially contained within outer housing 28 of IMD 14. As described in further detail below, lead connection assembly 40 includes a first electrical connector that mechanically couples at least one of the leads 18, 20, 22 to IMD 14 and electrically connects at least one of the leads 18, 20, 22 to the first therapy module within housing 28. Lead connection assembly 40 further includes a second electrical connector that mechanically couples lead 16 to IMD 14 and electrically connects lead 16 to the second therapy module within housing 28. For example, a proximal end of each of leads 16, 18, 20, 22 may be both electrically and mechanically coupled to lead connection assembly 40 of IMD 14 either directly or indirectly (e.g., via a lead extension). Electrical conductors disposed in the respective lead body may electrically connect stimulation electrodes (and sense electrodes, if present) of leads 16, 18, 20, 22 to either the first or second therapy modules within IMD 14 via lead connection assembly 40. Lead connection assembly 40 may also be referred to as a header or a connector block.

While the disclosure primarily describes leads as being directly connected to lead connection assembly 40, in other examples, leads, such as leads 16, 18, 20, 22, may be indirectly mechanically and electrically connected to lead connection assembly 40 via one or more lead extensions. A lead extension may effectively elongate a lead. In addition, in some examples, a bifurcated or trifurcated lead extension may be useful for mechanically and electrically connecting more than one lead to a common electrical connector of lead connection assembly 40.

The first and second electrical connectors of lead connection assembly 40 are configured to mate with a proximal portion of a corresponding lead or lead extension. The first and second electrical connectors of lead connection assembly 40 are configured to help prevent electrical stimulation from being inadvertently delivered to an incorrect tissue site within patient 12. For example, the first electrical connector may be configured such that it is substantially incompatible with lead 16 in order to prevent lead 16 from inadvertently being electrically connected to the first therapy module. Similarly, the second electrical connector may be configured such that it is substantially incompatible with one or more of leads 18, 20, 22 in order to prevent the one or more of leads 18, 20, 22 from being electrically connected to the second therapy module. The incompatibility between lead 16 and the first electrical connector of lead connection assembly 40 and between leads 18, 20, 22 and the second electrical connector of lead connection assembly 40 may be achieved via different techniques, such as incompatible physical characteristics (e.g., incompatible geometries), incompatible electrical contact arrangements, and/or incompatible sizes, as described in further detail below.

When leads 18, 20, 22 are properly connected to the first therapy module within IMD 14, the first therapy module of IMD 14 delivers at least one of pacing, cardioversion or defibrillation stimulation to heart 26 by implantable medical leads 18, 20, 22, and more particularly, via one or more stimulation electrodes carried by leads 18, 20, 22. Similarly, when lead 16 is properly connected to the second therapy module within IMD 14, the second therapy module delivers electrical stimulation (e.g., in the form of electrical pulses or a continuous signal) to a nonmyocardial or a nonvascular cardiac tissue site. In the example shown in FIG. 1, the second therapy module delivers electrical stimulation to a tissue site proximate spinal cord 44 via one or more stimulation electrodes carried by lead 16.

In some examples, IMD 14 also includes one or more housing electrodes, which may be formed integrally with an outer surface of hermetically-sealed housing 28 of IMD 14 or otherwise coupled to housing 28. In some examples, the housing electrode may be defined by an uninsulated portion of an outward facing portion of housing 28. Other divisions between insulated and uninsulated portions of housing 70 may be employed to define two or more housing electrodes. In some examples, such as the example shown in FIG. 1, the housing electrode may comprise substantially all of housing 28. In other examples, one or more electrodes may be embedded into an insulating casing that surrounds the outer surface of housing 28 or otherwise attached to outer housing 28 of IMD 14. Any of the electrodes of leads 16, 18, 20, 22 may be used for unipolar sensing or stimulation in combination with the one or more housing electrodes.

As shown in FIG. 1, therapy system 10 also includes programmer 24. In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display.

A user, such as a physician, technician, or other clinician, may interact with programmer 24 to communicate with IMD 14. For example, the user may interact with programmer 24 to retrieve physiological or diagnostic information from IMD 14. A user may also interact with programmer 24 to program IMD 14, e.g., select values for operational parameters for one or more of the stimulation therapies delivered by IMD 14. For example, the user may use programmer 24 to retrieve information from IMD 14 regarding the rhythm of heart 26, trends therein over time, or tachyarrhythmia episodes. As another example, the user may use programmer 24 to retrieve information from IMD 14 regarding other sensed physiological parameters of patient 12, such as electrical depolarization/repolarization signals from heart 26 (referred to as "electrogram" or EGM), intracardiac or intravascular pressure, activity, posture, respiration, or thoracic impedance. As another example, the user may use programmer 24 to retrieve information from IMD 14 regarding the performance or integrity of IMD 14 or other components of system 10 corresponding to the first stimulation therapy, such as leads 16, 18, 20, and 22, or a power source of IMD 14.

The user may use programmer 24 to program a therapy progression, select electrodes used to deliver defibrillation pulses, select waveforms for the defibrillation pulse, or select or configure a fibrillation detection algorithm for IMD 14. The user may also use programmer 24 to program aspects of other therapies provided by IMD 14, such as cardioversion, pacing or other electrical stimulation therapies. For example, with the aid of programmer 24, a user may select therapy parameters for the pacing, cardioversion, and/or defibrillation therapy delivered by leads 18, 20, 22, and/or the stimulation therapy delivered by lead 16. The stimulation therapy parameters may include, for example, an electrode combination, a current or voltage amplitude, and a frequency of stimulation signals to be delivered to patient 12, and, in the case of stimulation pulses, a pulse width and a pulse rate.

An electrode combination may include a selected subset of one or more electrodes located on implantable leads 16, 18, 20, 22 that are coupled to IMD 14. The electrode combination may also refer to the polarities of the electrodes in the selected subset. By selecting values for a slew rate, amplitude, frequency (e.g., pulse rate in the case of stimulation pulses), and pulse duration (e.g., pulse width in the case of stimulation pulses), the clinician can attempt to generate an efficacious therapy for patient 12 that is delivered via the selected electrode subset. In addition, at least with respect to lead 16, by selecting particular electrode combinations, a clinician may target particular anatomic structures within patient 12.

In some examples, the user may activate certain features of IMD 14 by entering a single command via programmer 24, such as depression of a single key or combination of keys of a keypad or a single point-and-select action with a pointing device. With the aid of programmer 24 or another computing device, a user may select values for therapy parameters for the second stimulation therapy generated and delivered by IMD 14. The values for the therapy parameters of the second stimulation therapy may be organized into a group of parameter values referred to as a "therapy program" or "therapy parameter set." "Therapy program" and "therapy parameter set" are used interchangeably herein.

Programmer 24 may communicate with IMD 14 via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 14 implant site in order to improve the quality or security of communication between IMD 14 and programmer 24.

Figure 2:
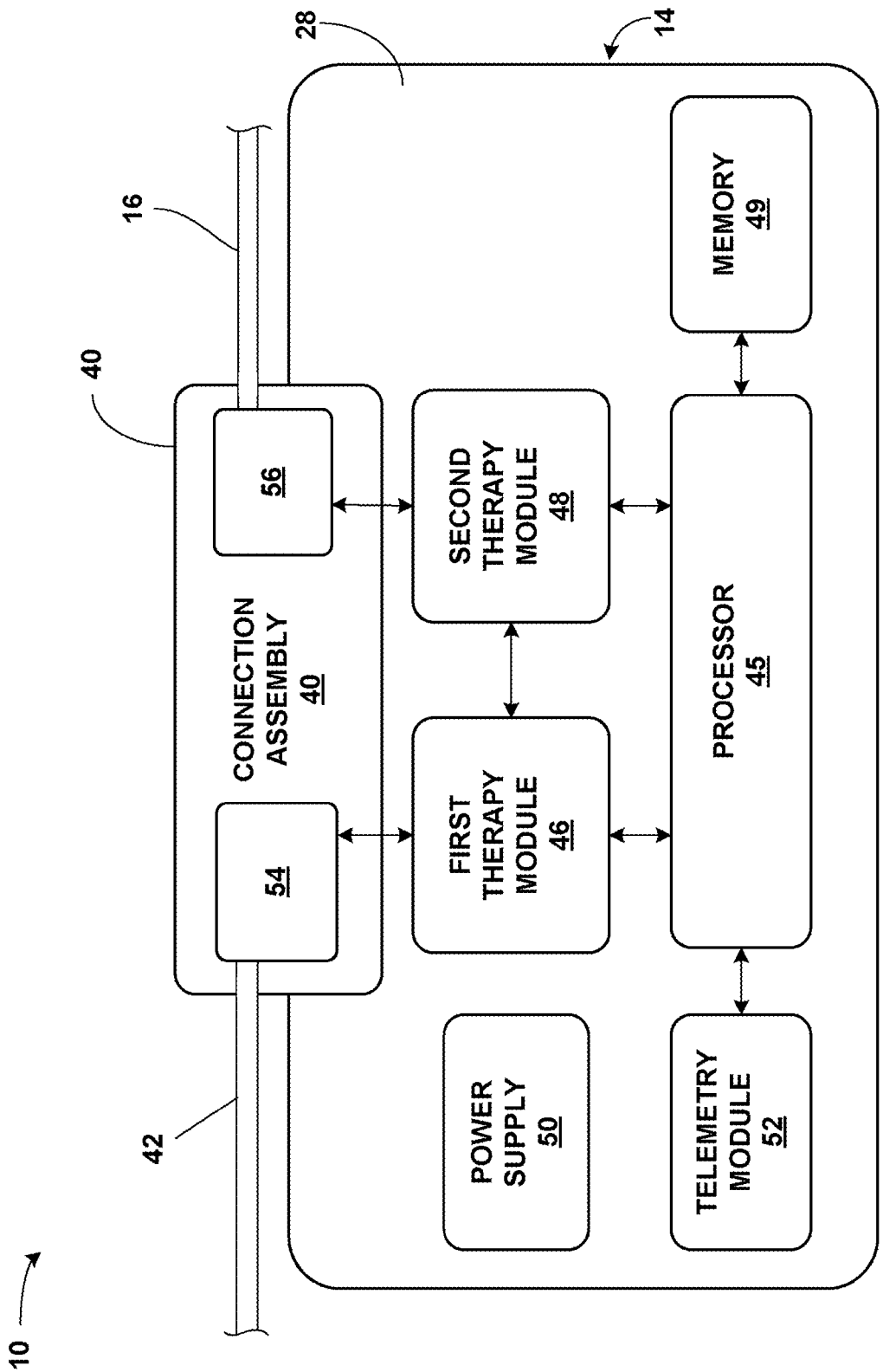
FIG. 2 is a functional block diagram illustrating the IMD of FIG. 1.

FIG. 2 is a functional block diagram illustrating example therapy system 10 including IMD 14, lead connection assembly 40, lead 42, and lead 16. Lead 42 may be any one or more of leads 18, 20, 22 or a lead extension electrically and mechanically coupled to one or more of leads 18, 20, 22. Although FIG. 2, as well as FIGS. 3-7, illustrate lead connection assembles configured to receive two leads, in other examples, lead connection assemblies in accordance with the disclosure may be configured to receive any suitable number of leads, such as one, two, three, four or more.

As shown in FIG. 2, IMD 14 includes processor 45, first therapy module 46, second therapy module 48, memory 49, power supply 50, and telemetry module 52. Memory 49 may include computer-readable instructions that, when executed by processor 45, cause processor 45 to perform various functions attributed to processor herein. Memory 49 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 45 may include any one or more of a microprocessor, a controller, a digital signal processor (DSP), an application specific integrated circuit (ASIC), a field-programmable gate array (FPGA), or equivalent discrete or integrated logic circuitry. In some examples, processor 45 may include multiple components, such as any combination of one or more microprocessors, one or more controllers, one or more DSPs, one or more ASICs, or one or more FPGAs, as well as other discrete or integrated logic circuitry. The functions attributed to processor 45 herein may be embodied as software, firmware, hardware or any combination thereof. Processor 45 may control first and second therapy modules 46, 48, respectively, to generate and deliver stimulation therapy to patient 12 according to a selected one or more of therapy programs, which may be stored in memory 49. Specifically, processor 45 may control the first and second therapy modules 46, 48, respectively to generate electrical signals with the amplitudes, pulse widths, frequency, or electrode polarities specified by the selected one or more therapy programs.

First therapy module 46 and second therapy module 48 may each include signal generators in order to generate the stimulation signals for delivery to patient 12. First therapy module 46 may be configured generate and deliver electrical stimulation signals of a first stimulation therapy type to patient 12 via lead 42. For example, first therapy module 46 may generate and deliver at least one of pacing, cardioversion or defibrillation therapy to heart 26 of patient 12 via lead 42. If first therapy module 46 is configured to generate and deliver defibrillation pulses to heart 26, first therapy module 46 may include a high voltage charge circuit and a high voltage output circuit. If first therapy module 46 is configured to generate and deliver pacing pulses to heart 26, processor 45 may include pacer timing and control module, which may be embodied as hardware, firmware, software, or any combination thereof. The pacer timing and control module may comprise a dedicated hardware circuit, such as an ASIC, separate from other processor 45 components, such as a microprocessor, or a software module executed by a component of processor 45, which may be a microprocessor or ASIC. The pacer timing and control module may be used by processor 45 to time the delivery of pacing pulses to heart 26.

Second therapy module 48 may be configured to generate and deliver electrical stimulation signals of a second stimulation therapy type to patient 12 via lead 16, where the second stimulation therapy type is different than the first stimulation therapy type. For example, second therapy module 48 may generate and deliver electrical stimulation therapy (e.g., neurostimulation) to a nonmyocardial tissue site (e.g., a tissue site proximate a nerve and/or an extravascular tissue site not proximate a nerve) or a nonvascular cardiac tissue site (e.g., a cardiac fat pad) via lead 16.

First therapy module 46 and second therapy module 48 may be electrically coupled to one or more electrodes of the respective lead 42, 16 via conductors of the respective lead 42, 16, or, in the case of a housing electrode, via an electrical conductor disposed within housing 28 of IMD 14. Lead 42 may be, for example, any one of leads 18, 20, 22 of therapy system 10 shown in FIG. 1. In some examples, first therapy module 46 is configured to receive leads 18, 20, 22, rather than a single lead 42, as shown in FIG. 2. In some examples, first therapy module 46 may deliver defibrillation shocks to heart 26 via at least two electrodes coupled to lead 42 or housing 28. First therapy module 46 may deliver pacing pulses via the housing electrode, ring electrodes coupled to lead 42, respectively, and/or helical electrodes of lead 42. In some examples, first therapy module 46 may deliver pacing, cardioversion, or defibrillation stimulation in the form of electrical pulses. In other examples, first therapy module 46 may deliver one or more of these types of stimulation in the form of other signals, such as sine waves, square waves, or other substantially continuous time signals.

Second therapy module 48 may be configured to generate and deliver second electrical stimulation therapy to a nonmyocardial tissue site, such as, e.g., an extravascular tissue site and/or tissue site proximate to a nerve, e.g., spinal cord 44, via at least two electrodes coupled to lead 16 and/or housing 28.

First and/or second therapy module 46, 48 may include a switch module, and processor 45 may use the switch module to select, e.g., via a data/address bus, which of the available electrodes of housing 28 and leads 16, 42 are used to deliver electrical stimulation. The switch module may include a switch array, switch matrix, multiplexer, or any other type of switching device suitable to selectively couple stimulation energy to selected electrodes. In other examples, however, first and/or second therapy module 46, 48 may independently deliver stimulation to one or more electrodes without a switch matrix.

In some examples first and second therapy modules 46, 48, respectively, may share one or more components utilized to operate as described herein. For example, in some cases, first therapy module 46 and second therapy module 48 may share a switch module. In addition, in some examples, first and second therapy modules 46, 48, respectively, may include components dedicated to only a single respective therapy module. For example, first and second therapy modules 46, 48, respectively, may have respective processors and/or memories.

Although not shown in FIG. 2, IMD 14 may also include a sensing module that monitors signals from at least one of the electrodes of leads 16, 42 and/or housing 28 in order to monitor electrical activity of heart 26, e.g., via an EGM signal. In some examples, the sensing module may include one or more sensing channels, each of which may comprise an amplifier. Under the control of processor 45, the switch module of the sensing module may couple the outputs from the selected electrodes to one of the sensing channels. The sensed electrical activity of heart 26 may be used to control the timing of the delivery of pacing, cardioversion or defibrillation shocks by first therapy module 46. For example, processor 46 may employ any suitable arrhythmia detection methodologies in order to detect an arrhythmia based on electrical cardiac signals sensed by the sensing module, and the detection of an arrhythmia may be used to control the delivery of defibrillation shocks by first therapy module 46, e.g., to attempt to terminate the detected arrhythmia.

Telemetry module 52 includes any suitable hardware, firmware, software or any combination thereof for communicating with another device, such as programmer 24 (FIG. 1). Under control of processor 45 of IMD 14, telemetry module 52 may receive downlink telemetry from and send uplink telemetry to programmer 24 with the aid of an antenna, which may be internal and/or external. IMD 14 may provide the data to be uplinked to programmer 24 and the control signals for the telemetry circuit within telemetry module 52 e.g., via an address/data bus. In some examples, telemetry module 52 may provide received data to a processor of IMD 14 via a multiplexer.

The various components of IMD 14 may be coupled to power supply 50, which may include a rechargeable or non-rechargeable battery. A non-rechargeable battery may be selected to last for several years, while a rechargeable battery may be inductively charged from an external device, e.g., on a daily or weekly basis. In other examples, power supply 50 may be powered by proximal inductive interaction with an external power supply carried by patient 12.

As previously described, IMD 14 may be mechanically coupled to leads 16, 42 and electrically coupled to electrodes of leads 16, 42 via lead connection assembly 40. As shown in FIG. 2, lead connection assembly 40 includes first electrical connector 54 and second electrical connector 56, which are configured to receive leads 42, 16, respectively. When lead 42 is properly connected to first electrical connector 54, electrical stimulation generated by first therapy module 46 may be conducted from first therapy module 46 to heart 26 of patient 12 via conductors and electrodes of lead 42. Similarly, when lead 16 is properly connected to second electrical connector 56, electrical stimulation generated by second therapy module 48 may be conducted from second therapy module 48 to spinal cord 44 (or another tissue site) via conductors and electrodes of lead 16. In this manner, IMD 14 may be configured to deliver both two different types of electrical stimulation therapy to patient 12.

Lead connection modules or assemblies illustrated and described herein with respect to FIGS. 2-7 include two electrical connectors for ease of illustration and description. In other examples, lead connection modules or assemblies described herein may include any suitable number of electrical connectors to electrically couple any suitable number of leads to therapy modules 46, 48. For example, as shown in FIG. 1, therapy system 10 may include four leads 16, 18, 20, 22, whereby three leads 18, 20, 22 are used to deliver cardiac rhythm therapy to heart 26 of patient 12. Accordingly, in some examples, lead connection assembly 40 may include additional electrical connectors that are configured to receive additional leads of therapy system 10, e.g., such that lead connection assembly 40 may electrically couple electrodes of leads 18, 20, 22 to first therapy module 46 and/or electrodes of an additional lead to therapy module 48. In other examples, one or both electrical connectors 54, 56 may be configured to receive more than one lead.

First electrical connector 54 and second electrical connector 56 may be any suitable type of electrical connector capable of electrically and mechanically coupling lead 42 and lead 16, respectively, to IMD 14. For example, first electrical connector 54 and second electrical connector 56 may each be configured as receptacles configured to receive a proximal end of the respective lead 42, 16 (or a lead extension). In some examples, the proximal end of a lead (or lead extension) may be physically secured in the corresponding electrical connector receptacle via a set screw, while in other examples, the proximal end of each lead (or lead extension) may mate with the receptacle in a self-securing manner. In some examples, first and/or second electrical connectors 54 and 56 are Bayonet Neill Concelman (BNC) electrical connectors or have configurations similar to BNC electrical connectors, which are physically configured to mate with the respective lead 42, 16. In addition, in some examples, first and/or second electrical connectors 54 and 56 are threaded Neill Concelman (TNC) type electrical connectors or have configurations (e.g., bayonet mount style) similar to TNC electrical connectors, which are configured to physically mate with and receive leads 42, 16 in a threaded configuration. In other examples, first and/or second electrical connectors 54 and 56 are connected to leads 42, 16 without the aid of a set screw, such as with the aid of a lever that pushes leads 42, 16 into physical and electrical connection with electrical contacts within the respective electrical connectors 54, 56.

In some examples, during implantation of therapy system 10 in patient 12, a clinician may inadvertently attempt to introduce lead 16 into first electrical connector 54 and/or attempt to introduce lead 42 may inadvertently introduced into second electrical connector 56. In some cases, it may be undesirable for lead 16 to deliver electrical stimulation from first therapy module 46 to a nonmyocardial tissue site or a nonvascular cardiac tissue site, e.g., a tissue site proximate a nerve or an extravascular tissue site that may not be proximate a nerve. In addition, it may be undesirable for lead 42 to deliver electrical stimulation generated by second therapy module 48 to heart 26.

In some examples, the delivery of electrical stimulation therapy that is configured for delivery to spinal cord 44, or another tissue site other than vascular tissue of heart 26, e.g., another tissue site proximate a nerve or an extravascular tissue site, may cause one or more undesirable physiological responses if delivered to heart 26. For example, the stimulation therapy generated by second therapy module may include second electrical stimulation signals including a frequency ranging from approximately 1 Hertz (Hz) to approximately 100 Hz, such as, approximately 10 Hz to approximately 100 Hz. The delivery of electrical stimulation signals having such a frequency to heart 26 may induce an arrhythmia, such as a ventricular fibrillation, which may be undesirable.

In general, the configuration of lead connection assembly 40 may provide a safeguard against the unintended delivery of electrical stimulation signals generated by second therapy module 48 to heart 26 of patient 12 via lead 42. In some examples, second electrical connector 56 of connector assembly 40 may be physically incompatible with lead 42, e.g., based on the relative geometry or sizes of second electrical connector 56 and lead 42. In some examples, the incompatibility substantially prevents lead 42 from being introduced into the receptacle defined by second electrical connector 56, e.g., because of size or geometrical constraints.

In other examples, in addition to or instead of the size or geometrical constraints, second electrical connector 56 and lead 42 may be substantially electrically incompatible. For example, the configuration of second electrical connector 56 may prevent at least some of the electrodes of lead 42 from being electrically connected to second electrical connector 56. This may be accomplished, for example, by different arrangements of electrical contacts on lead 42 and within second electrical connector 56 or with an electrical component other than the electrical contacts that electrically connects to a corresponding portion of the respective lead 16, 42. In some examples, a lack of an electrical connection between the electrical component of the electrical connector 54, 56 and the respective lead 42, 16 may substantially prevent therapy modules 46, 48 from delivering therapy via the electrodes of the respective lead 42, 16. In this way, the incompatibility between second electrical connector 56 and lead 42 may help prevent lead 42 from being inadvertently electrically coupled to second therapy module 48 via second electrical connector 56.

In addition, in some examples, first electrical connector 54 of connector assembly 40 may be incompatible with lead 16 in order to provide a safeguard against the unintended delivery of electrical stimulation signals generated by first therapy module 46 to a tissue site within patient 12 via lead 16. For example, first electrical connector 54 may define a receptacle that is configured to prevent lead 16 from being introduced into the receptacle, e.g., because of size or geometrical constraints. In other examples, in addition to or instead of the size or geometrical constraints, the incompatibility between first electrical connector 54 and lead 16 prevents at least some of the electrodes of lead 16 from being electrically connected to first electrical connector 54. This may be referred to herein as electrical incompatibility.

Figure 4:
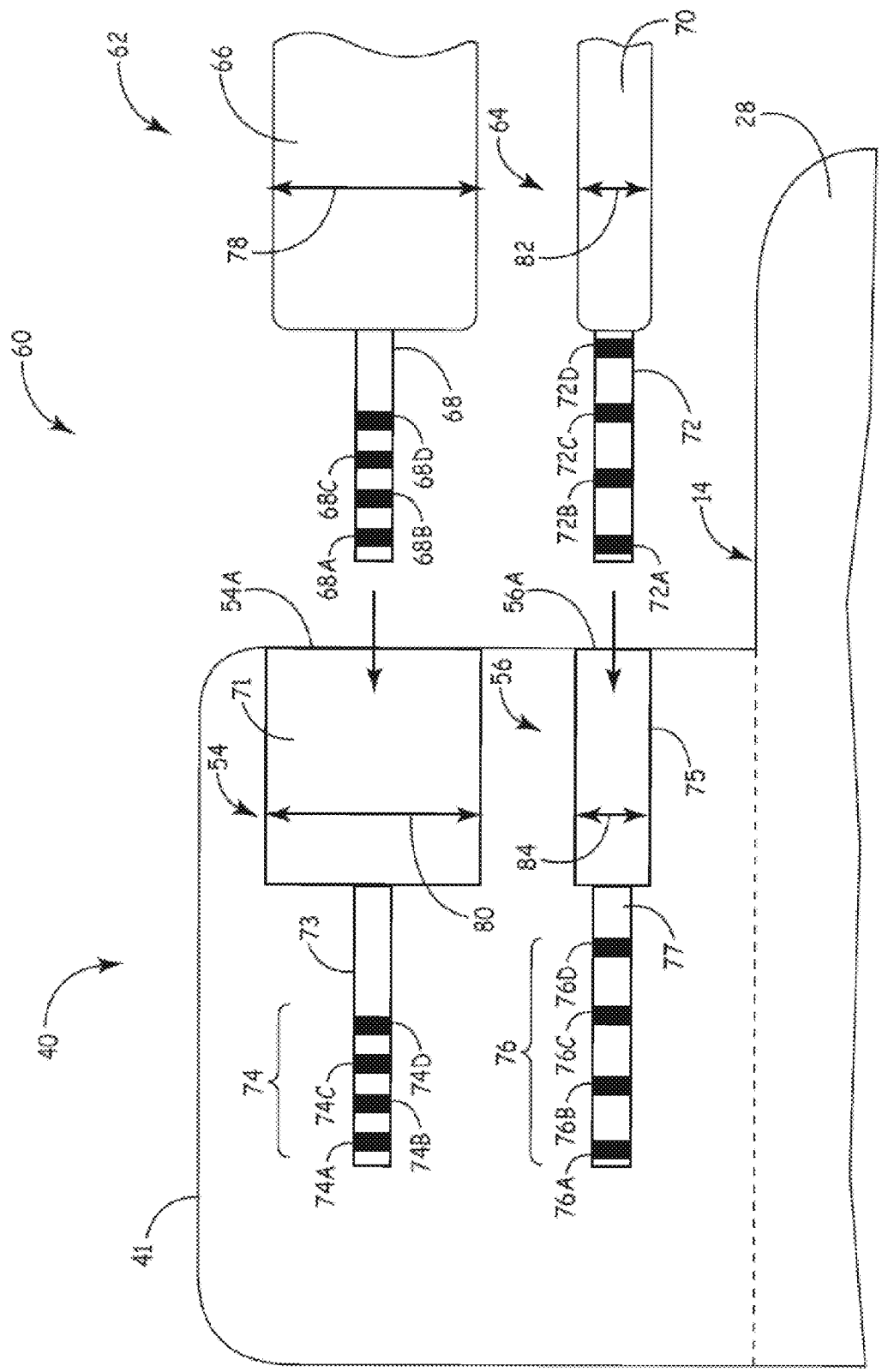
FIG. 4 is a conceptual diagram illustrating a cross-sectional view of a portion of the example therapy system of FIG. 3.

In addition to or instead of achieving lead 42 incompatibility with second electrical connector 56 and/or lead 16 incompatibility with first electrical connector 54 via different geometrical or sizes, or different electrical contact arrangements, which are described in further detail with respect to FIG. 4, leads 16, 42 and electrical connectors 54, 56 may be marked with a visible identifier that helps a user associate leads 42, 16 with the proper electrical connector 54, 56, respectively. In some examples, at least a portion of lead 42 may be marked with a first color (e.g., via a colored band embedded or otherwise incorporated or attached to lead 42) and first electrical connector 54 may also be marked with the first color. As an example, first electrical connector 54 may have a color band within or outside of a perimeter of an opening configured to receive lead 42. The color coding may indicate to a user that first lead 42 should be introduced into first electrical connector 54. Thus, during assembly of therapy system 10, the user may match the color coding on lead 42 with the color coding on lead connection assembly 40 in order to electrically couple lead 42 to the proper therapy module. Similarly, at least a portion of lead 16 may be marked with a second color and second electrical connector 54 may also have portion with the second color. Alphanumeric identifiers, symbolic identifiers (e.g., geometric symbols) or other types of visible identifiers may also be used to associate leads 16, 42 with the respective electrical connectors 56, 54.

In the example shown in FIG. 2, electrical connectors 54, 56 define openings that permit leads 42, 16, respectively, to extend away from housing 28 of IMD 14 in substantially different directions. In particular, in the example shown in FIG. 2, leads 42, 46 extend from housing 28 in substantially opposite directions. In other examples, leads 42, 46 may extend from housing 28 in any suitable directions that are different from each other, such as, but not limited to orthogonal directions. As described with respect to FIG. 8, this configuration of lead connection assembly 40 may be more conducive to implanting therapy system 10 in patient 12.

Figure 3:
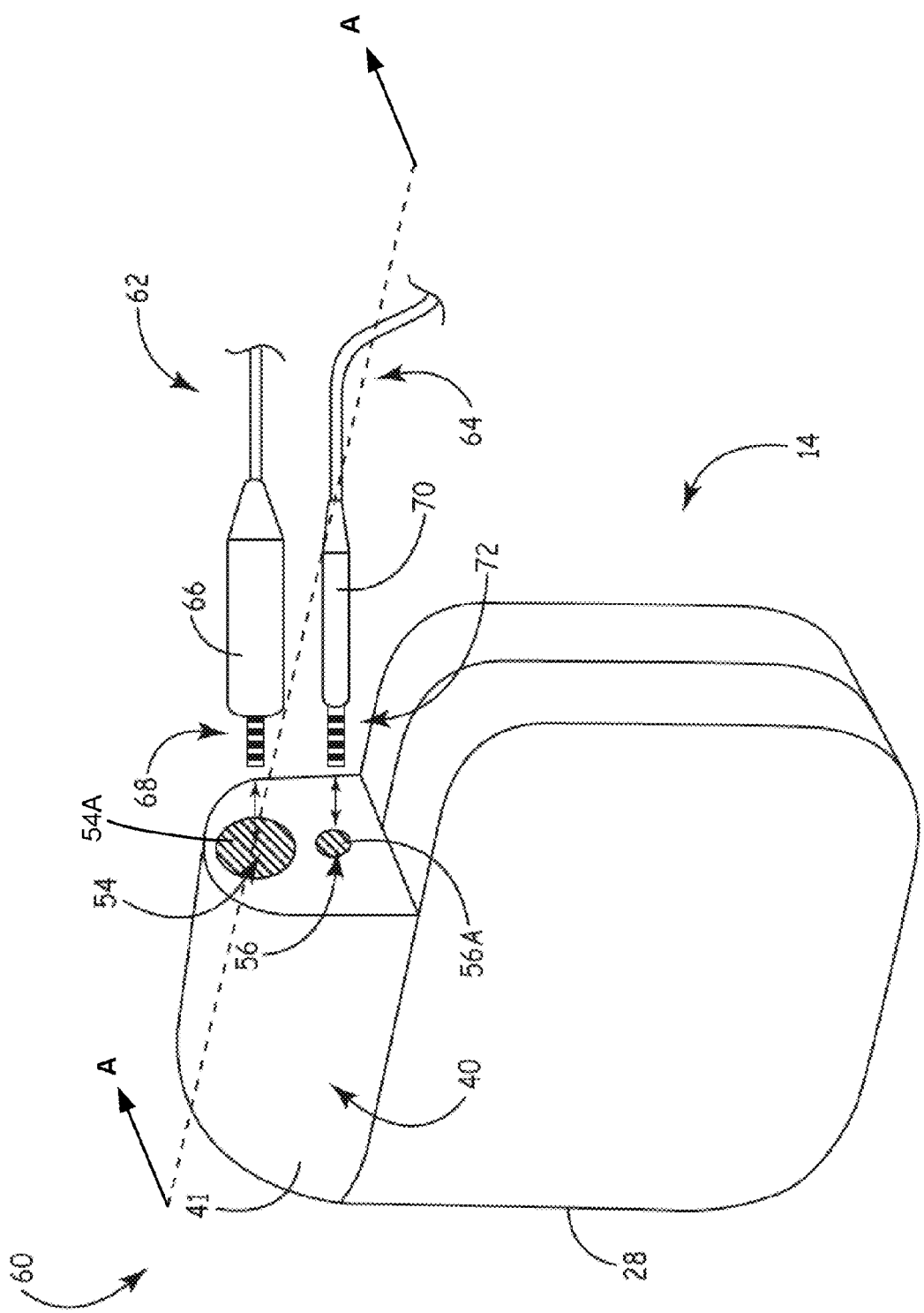
FIG. 3 is a conceptual diagram illustrating a perspective view of an example therapy system.

FIG. 3 is a conceptual diagram illustrating a perspective view of example therapy system 60, which includes IMD 14, lead connection assembly 40, first lead 62, and second lead 64. IMD 14 and lead connection assembly 40 are described above with respect to FIGS. 1 and 2. Lead 62 may be configured to deliver electrical stimulation from first therapy module 46 (FIG. 2) to heart 26 (FIG. 1) of patient 12, and lead 64 may be configured to deliver electrical stimulation from second therapy module 48 (FIG. 2) to a nonmyocardial tissue site or a nonvascular cardiac tissue site within patient 12. Thus, in some examples, first lead 62 may be the same or similar to that of one or more of leads 18, 20, 22 of FIG. 1 and second lead 64 may be the same or similar to that of lead 16 of FIG. 1.

FIG. 3 illustrates an example lead connection assembly 40 in which first and second electrical connectors 54, 56, respectively, have one or more features that help prevent the inadvertent delivery of electrical stimulation from second therapy module 48 (FIG. 2) to heart 26 of patient 12. That is, first and second electrical connectors 54, 56, respectively, have one or more features that help prevent first lead 62 from being electrically coupled to second therapy module 48 via second electrical connector 56.

Lead connection assembly 40 is configured to connect first and second leads 62, 64 to first and second therapy modules 46, 48, respectively, enclosed within housing 28 of IMD 14. Leads 62, 64 may be introduced into openings 54A, 56A, respectively, defined by housing 41 of lead connection assembly 40. In FIG. 3, first lead 62 and second lead 64 are disconnected from lead connection assembly 40, but aligned with respective openings 54A, 56A. In the example shown in FIG. 3, first electrical connector 54 is configured to electrically and mechanically couple first lead 62 to first therapy module 46, such that cardiac rhythm therapy generated by first therapy module 46 may be delivered to heart 26 of patient 12 via one or more electrodes of first lead 62. Second electrical connector 56 is configured to electrically and mechanically couple second lead 64 to second therapy module 48 such that electrical stimulation signals generated by second therapy module 48 may be delivered to spinal cord 44 of patient 12 via one or more electrodes of second lead 64.

As shown in FIG. 3, first electrical connector 54 and second electrical connector 56 may be receptacle-type electrical connectors. For example, each electrical connector 54, 56 may define a recess in housing 41 lead connection assembly 40 that is configured to receive a proximal portion of the respective lead 62, 64. In the example shown in FIG. 3, the proximal portion of first lead 62 includes first plug member 66 and first electrical contact portion 68. First electrical contact portion 68 includes a first set of electrical contacts that are electrically coupled to electrodes of lead 62 via conductors within a lead body of lead 62. At least a portion of first electrical contact portion 68 may be introduced into first electrical connector 54 in a manner that electrically couples electrodes of lead 62 to first therapy module 46 (FIG. 2) via the first set of electrical contacts. Similarly, second lead 64 includes second plug structure 70 and second electrical contact portion 72. Second electrical contact portion 72 and at least a portion of second plug structure 70 may be introduced into second electrical connector 56 in a manner that electrically couples electrodes of second lead 64 to second therapy module 48 (FIG. 2) via a second set of electrical contacts that are located on second electrical contact portion 72.

In the example shown in FIG. 3, second electrical connector 56 of lead connection assembly 40 is incompatible with first lead 62. For example, as described in greater detail with respect to FIG. 4, the physical dimensions of second electrical connector 56 and first plug member 66 and/or first electrical contact portion 68 may substantially discourage first lead 62 from being introduced into opening 56A of second electrical connector 56. For example, in the example shown in FIG. 3, first plug member 66 of first lead 62 has a larger cross-sectional size (measured along a direction substantially orthogonal to a longitudinal axis of lead 62) than an opening 56A, such that first lead 62 may not be easily introduced into second electrical connector 56. In this way, first lead 62 may be considered to be physically incompatible with second electrical connector 56.

The difference in size between first plug member 66 of first lead 62 and opening 56A of second electrical connector 56 may both visually and tactilely indicate to a user, such as a clinician, that lead 62 is not intended to be introduced into second electrical connector 56. For example, the user may be alerted to the incompatibility between first lead 52 and second electrical connector 56 based on a visual assessment of the different sizes, and, in some examples, as well as based on the different visual indicia on lead 62 and electrical connector 56. As another example, the user may be alerted to the incompatibility between first lead 52 and second electrical connector 56 based on the resistance first lead 62 exerts when the user attempts to introduce first lead 62 into second electrical connector 56.

FIG. 4 is a conceptual diagram illustrating a cross-sectional view of a portion of system 60 of FIG. 3. In particular, FIG. 4 illustrates a cross-sectional view of IMD 14, electrical connector assembly 40, first lead 62, and second lead 64 taken along line A-A in FIG. 3. First electrical connector 54 of lead connection assembly 40 may include first portion 71 and second portion 73, which defines a plurality of electrical contacts 74A-74D (collectively "electrical contacts 74"). Electrical contacts 74 are electrically coupled to first therapy module 46 (not shown), e.g., via conductive elements that extend between electrical contacts 74 and first therapy module 46. Opening 54A defined by housing 41 of lead connection assembly 40 provides access to first portion 71 and second portion 73 of first electrical connector 54, through which lead 62 may be introduced. First portion 71 and second portion 73 may define, for example, a receptacle of first electrical connector 54.

Second electrical connector 56 of lead connection assembly 40 may include first portion 75 and second portion 77, which may define a receptacle of second electrical connector 56. Second portion 77 of second electrical connector 56 includes a plurality of electrical contacts 76A-76D (collectively "electrical contacts 76") that are electrically coupled to second therapy module 48 (not shown), e.g., via conductive elements that extend between electrical contacts 76 and second therapy module 48. Opening 56A defined by housing 41 of lead connection assembly 40 provides access to first portion 75 and second portion 77 of second electrical connector 56, through which lead 64 may be introduced.

First lead 62 is compatible with first electrical connector 54. For example, the physical dimensions of first electrical connector 54 permit first electrical contact portion 68 and at least a portion of first plug member 66 of first lead 62 to be introduced into through openings 54A and into first electrical connector 54. In the example shown in FIG. 4, diameter 78 of first plug member 66 is substantially equal to or less than diameter 80 of first portion 71 of first electrical connector 54. Accordingly, when properly inserted, second portion 73 of first electrical connector 54 may receive first electrical contact portion 68 in a manner that electrically couples first lead 62 to first therapy module 46. That is, when lead 62 is properly introduced into first electrical connector 54, electrical contacts 68A-68D of lead 62 may contact electrical contacts 74A-74D, respectively, of second portion 74 of first electrical connector 54. In some examples, electrical contacts 68A-68D and electrical contacts 74A-74D have substantially similar surface areas, and when lead 62 is properly introduced into first electrical connector 54, electrical contacts 68A-68D and electrical contacts 74A-74D substantially align such that a majority of the surface areas (e.g., greater than 75%) of each of the electrical contacts 68A-68D is in contact with a majority of the surface area of a respective electrical contact 74A-74D.

As previously indicated, electrical contacts 68A-68D of lead 62 may be electrically coupled to a respective stimulation or sensing electrode of lead 62 via conductors within a lead body of lead 62. Thus, aligning electrical contacts 68A-68D of lead 62 with electrical contacts 74A-74D of first electrical connector 54 may electrically connect the electrodes of lead 62 with first therapy module 46, which is electrically connected to electrical contacts 74A-74D.

Second lead 64 is compatible with second electrical connector 56. For example, the physical dimensions of second electrical connector 56 permit second electrical contact portion 72 and at least a portion of second plug member 70 of second lead 64 to be introduced into second electrical connector 56 via opening 56A. In the example shown in FIG. 4, diameter 82 of second plug member 70 is less than or substantially equal to diameter 84 of first portion 75 of second electrical connector 56. Accordingly, when properly inserted, second portion 76 of second electrical connector 56 may receive second electrical contact portion 72 in a manner that electrically couples second lead 64 to second therapy module 48. When lead 64 is properly introduced into second electrical connector 56, electrical contacts 72A-72D of lead 64 may contact electrical contacts 76A-76D, respectively, of second portion 74 of second electrical connector 56. In some examples, electrical contacts 72A-72D and electrical contacts 76A-76D may have substantially similar surface areas, and when lead 64 is properly introduced into second electrical connector 56, electrical contacts 72A-72D and electrical contacts 76A-76D may substantially align such that a majority of the surface areas (e.g., greater than 75%) of each of the electrical contacts 72A-72D is in contact with a majority of the surface area of a respective electrical contact 76A-76D.

As previously indicated, electrical contacts 72A-72D of lead 64 may be electrically coupled to a respective stimulation or sensing electrode of lead 64 via conductors within a lead body of lead 64. Thus, aligning electrical contacts 72A-72D of lead 64 with electrical contacts 76A-76D of second electrical connector 56 may electrically connect the electrodes of lead 64 with second therapy module 48, which is electrically connected to electrical contacts 76A-76D.

As shown in FIGS. 3 and 4, first lead 62 is substantially incompatible with second electrical connector 56. For example, although first and second electrical contact portions conductors 68 and 72 may have similar dimensions, diameter 78 of first plug member 66 of first lead 62 is greater than diameter 84 of first portion 75 of second electrical connector 56, which helps prevent first electrical contact portion 68 from being introduced into second portion 77 of second electrical connector 56. In some examples, first lead 62 may be sized such that electrical contact portion 68 may be introduced into first portion 75 of second electrical connector 56. However, in such examples, electrical contacts 68A-68D of first lead 62 may not contact electrical contacts 76A-76D of second electrical connector 56 when electrical contact portion 68 is introduced into first portion 75 of second electrical connector 56. In this way, the incompatible configurations of second electrical connector 56 and first lead 62 help prevent electrical contacts 68A-68D of first lead 62 from electrically coupling to second therapy module 48 (FIG. 2), which is electrically coupled to electrical contacts 76 of second electrical connector 56. As a result, lead 62 may not deliver electrical stimulation signals generated by second therapy module 48 to heart 26 of patient 12.

Moreover, the difference in size between first plug member 66 and first portion 75 of second electrical connector 56 may indicate, e.g., to a clinician, that first lead 62 is not intended to be introduced into second electrical connector 56. This may further prevent inadvertent introduction of first lead 62 into second electrical connector 56. In addition, if lead 64 was introduced into first electrical connector 54, the loose fit between lead 64 and connector 54 would alert the clinician or other user that the leads 62, 64 may be reversed.

In the example shown in FIG. 4, another feature of lead connection assembly 40 that prevents the inadvertent delivery of electrical stimulation generated by second therapy module 48 (FIG. 2) to heart 26 of patient 12 is the configuration of electrical contacts 76 of second electrical connector 56 relative to the configuration of electrical contacts 68A-68D of first lead 62. As FIG. 4 illustrates, electrical contacts 68A-68D of lead 62 have a different relative spacing than electrical contacts 76A-76D of second electrical connector 56. Thus, even if the size of lead 62 permits electrical contact portion 68 of lead 62 to be introduced into second portion 77 of second electrical connector 56, at least some of electrical contacts 68A-68D may not align with or electrically connect with electrical contacts 76A-76D. In this way, an electrical connection between electrical contacts 68A-68D of lead 62 and electrical contacts 76A-76D may be minimized or even avoided, even if lead 62 is introduced into second electrical connector 56. The substantially incompatible electrical contact arrangement between lead 62 and second electrical connector 56 may be used instead of or in addition to the incompatible sizes.

In some examples, at least some of electrical contacts 68A-68D may at least partially contact electrical contacts 76A-76D, respectively, despite the different electrical contact arrangement (e.g., spacing). However, limited contact between at least some of electrical contacts 68A-68D, 76A-76D may still help minimize or even eliminate undesirable stimulation of heart 26 via electrical stimulation signals generated by second therapy module 48 (FIG. 2). For example, if one or two of electrical contacts 68A-68D fully contact a respective one of the electrical contacts 76A-76D, the intensity of stimulation delivered to heart 26 may be insufficient to generate undesirable physiological responses (e.g., an induced arrhythmia). As another examples, if one or more of electrical contacts 68A-68D partially contact one or more of electrical contacts 76A-76D, the intensity of stimulation delivered to heart 26 may be insufficient to generate undesirable physiological responses.

In some examples, each of the electrical contacts 68A-68D may be spaced from an adjacent electrical contact of lead 62 by a first distance of approximately 1 millimeters (mm) to about 6 mm, and each of electrical contacts 76A-76D may be spaced from an adjacent electrical contact of second electrical connector 56 by a second distance of approximately 1 mm to about 6 mm, where the first and second distances are different. Although FIG. 4 illustrates an example in which electrical contacts 76A-76D have a greater spacing relative to each other than electrical contacts 68A-68D, in other examples, electrical contacts 68A-68D may be spaced from each other by a greater distance than electrical contacts 76A-76D. In addition, electrical contacts 68A-68D, 76A-76D may not need to be spaced by an even distance. For example, electrical contacts 68A, 68B may be closer to each other than electrical contacts 68B, 68C.

In some examples, such as that shown in FIGS. 3 and 4, the size of second lead 64 may not necessarily be incompatible with first electrical connector 54, even if the size of first lead 62 is incompatible with second electrical connector 56. Diameter 80 of first portion 71 of first electrical connector 54 is greater than the diameter 82 of second plug member 70 of second lead 64, thereby permitting lead 64 to be introduced into first electrical connector 54. Thus, despite a difference in the dimensions of second lead 64 relative to first electrical connector 54, second plug 70 may be configured to be inserted into first electrical connector 54 in a manner that enables electrical contact portion 72 to be introduced into second portion 73 of first electrical connector 54. However, in some examples, the inadvertent delivery of at least one of pacing, cardioversion, or defibrillation therapy generated by first therapy module 46 (FIG. 2) to a nonmyocardial tissue site, e.g., an extravascular tissue site and/or site proximate a nerve, such as spinal cord 44, or a nonvascular cardiac tissue site may not cause the same nature and/or degree of undesirable side-effects as previously identified with respect to delivery of the second stimulation therapy to heart 26 of patient 12.

In the example shown in FIG. 4, electrical contacts 72A-72D of second lead 64 and electrical contacts 74A-74D of first electrical connector 54 have substantially different arrangements, such that even if electrical contact portion 72 of lead 64 is introduced into second portion 73 of first electrical connector 54, an electrical connection between first therapy module 46 (FIG. 2) and electrodes of lead 64 may not established, or at least minimized. In the example shown in FIG. 4, electrical contacts 72A-72D of second lead 64 are spaced from each other by a greater distance than the distance with which electrical contacts 74A-74D of electrical connector 54 are spaced from each other. In this way, second lead 64 and first electrical connector 54 may be incompatible.

Figure 5:
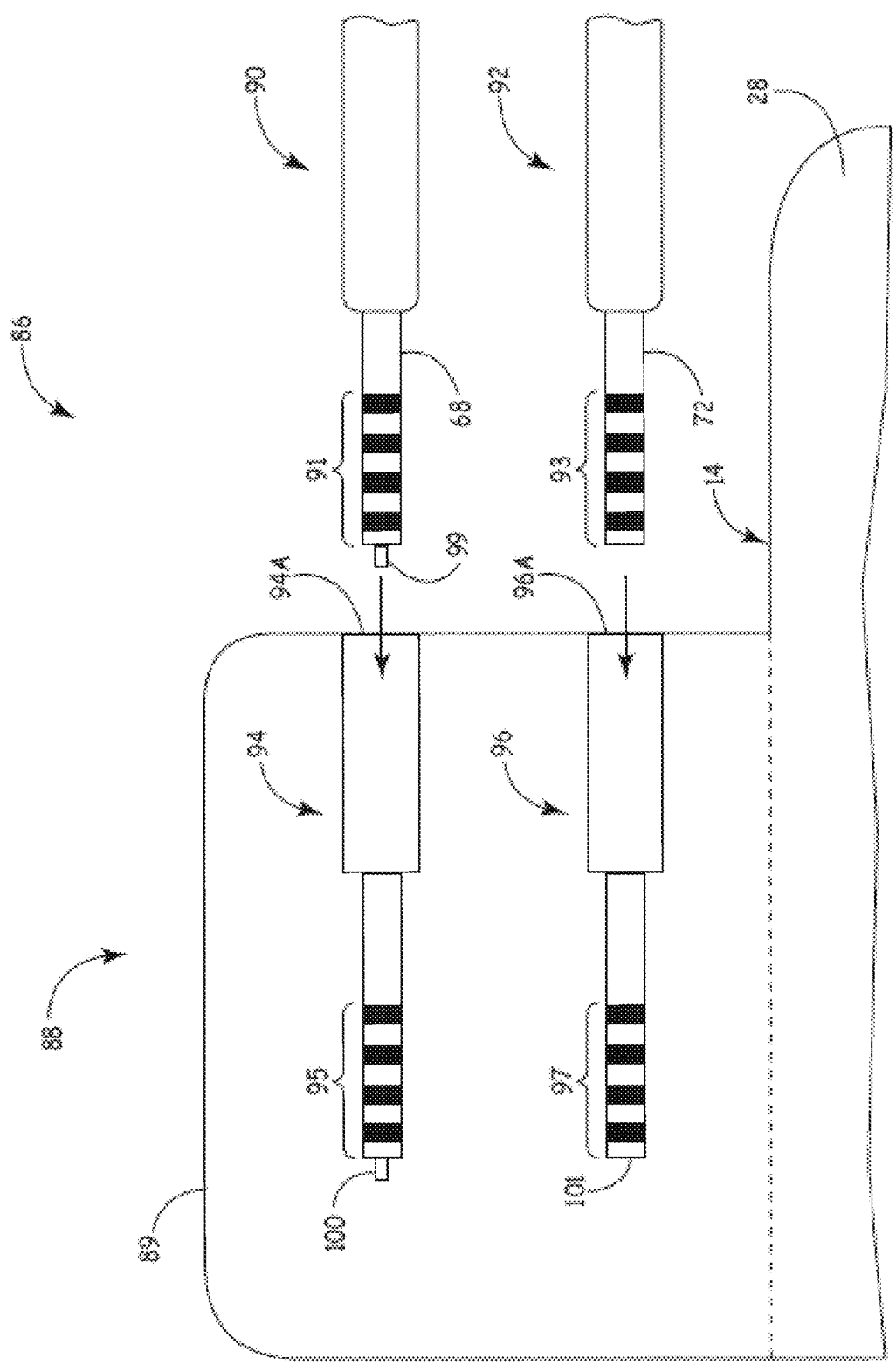
FIG. 5 is a conceptual diagram illustrating a cross-sectional view of a portion of another example therapy system that includes an electrical connector that is substantially physically incompatible with a lead.

FIG. 5 is a conceptual diagram illustrating a cross-sectional view another example therapy system 86, which includes IMD 14, lead connection assembly 88, first lead 90, and second lead 92. Lead connection assembly 88 may be connected to IMD 14, e.g., as described with respect to lead connection assembly 40 of FIG. 1.

Lead connection assembly 88 includes first electrical connector 94 and second electrical connector 96, which have substantially similar sized openings 94A, 96A defined by housing 89 of lead connection assembly 88. First electrical connector 94 comprises a set of electrical contacts 95 that are electrically connected to first therapy module 46 (FIG. 2). First lead 90 may be introduced into first electrical connector 94 such that electrical contacts 91 of lead 90 substantially align with and contact electrical contacts 95 of electrical connector 94 in order to establish an electrical connection between first therapy module 46 and one or more stimulation and/or sensing electrodes of lead 90, which are electrically coupled to a respective one of the electrical contacts 91. In this way, first therapy module 46 may deliver at least one of pacing, cardioversion or defibrillation therapy to heart 26 (FIG. 1) of patient 12 via electrodes of first lead 90.

Second electrical connector 96 comprises a set of electrical contacts 97 that are electrically connected to second therapy module 48 (FIG. 2) of IMD 14. Second lead 92 may be introduced into second electrical connector 96 such that electrical contacts 93 of lead 92 may substantially align with and contact electrical contacts 97 of second electrical connector 96 in order to establish an electrical connection between second therapy module 48 and one or more stimulation and/or sensing electrodes of lead 92, which are electrically coupled to a respective one of the electrical contacts 93. In this way, second therapy module 48 may deliver stimulation therapy to a tissue site within patient 12 via electrodes of second lead 92.

The relative physical dimensions of the portions of first and second leads 90, 92, respectively, which may be received by first and second electrical connectors 94, 96, respectively, are substantially similar. Accordingly, the physical dimensions of first lead 90 do not prevent first lead 90 from being inserted into opening 96A of second lead connector 96 and, likewise, the physical dimensions of second lead 92 do not prevent second lead 92 from being inserted into opening 94A of first electrical connector 94.

In addition, in the example shown in FIG. 5, electrical contacts 91 of first lead 90 have a substantially similar arrangement as electrical contacts 97 of second electrical connector 96. Thus, lead 90 and second electrical connector 96 are configured such that electrical contacts 91 of first lead 90 may substantially align with and contact electrical contacts 97, thereby establishing an electrical connection between second therapy module 48 (FIG. 2) and lead 90. As described above, this may be undesirable because the delivery of electrical stimulation signals generated by second therapy module 48 may cause undesirable physiological responses by heart 26.

In order to help prevent first lead 90 from being introduced into second electrical connector 96, e.g., to prevent first lead 90 from delivering electrical stimulation signals generated by second therapy module 48 to heart 26, first lead 90 may include center pin 99. Center pin 99 may be configured to slide into hollow center bore 100 defined by first electrical connector 94 of lead connection assembly 88. Center pin 99 of lead 90 configures lead 90 such that it is substantially physically incompatible with second electrical connector 96. As shown in FIG. 5, when first lead 90 is introduced into second electrical connector 96, center pin 99 of lead 90 may contact wall 101, which prohibits lead 90 from being fully introduced into second electrical connector 96. Moreover, center pin 99 may interfere with the ability of electrical contacts 91 of first lead 90 to align with electrical contacts 97 of second electrical connector 96, thereby preventing the electrodes of first lead 90 from electrically connecting to second therapy module 48 (FIG. 2). Center pin 99 may also prevent alignment of one or more visible alignment markers associated with lead 90 and/or second electrical connector 96, which may indicate improper connection of lead 90 with second electrical connector 96.

In some examples, center pin 99 is an electrically conductive component of lead 90, and bore 100 includes an electrical contact. In such an example, lead 90 is only configured to deliver stimulation to patient 12 if center pin 99 makes electrical contact with lead 90. Processor 45 of IMD 14 (FIG. 2) may determine whether center pin 99 is in electrical contact with lead 90 prior to controlling therapy module 46 to deliver electrical stimulation to electrodes of lead 90. For example, processor 45 may determine an impedance of an electrical path including the center pin 99 and compare the impedance to a stored threshold value or a range of stored threshold values to determine whether the impedance indicates center pin 99 is in electrical contact with lead 90.

In some examples, second electrical connector 96 may be configured in a manner that does not allow delivery of electrical stimulation to patient via lead 90 unless all electrical contacts 91 of first lead 90 are in contact with electrical contacts 97 of second electrical connector 96. For example, although the spacing between adjacent electrical contacts 91 may be consistent with the spacing between adjacent electrical contacts 97 such that less than all of the individual contacts, e.g., three of the four contacts shown) may be brought fully into contact with one another when lead 90 is partially inserted in electrical connector 96, second electrical connector 96 may be configured in a manner that does not allow delivery of electrical stimulation via lead 90 unless each of the four electrical contacts 97 are in contact with the corresponding electrical contacts 91 of first lead 90. In this manner, even though electrical contacts 91 of first lead 90 may have substantially the same configuration of electrical contacts 97 of second lead connector 96, first lead 90 may still be prevented from electrically coupling to second therapy module 48 (FIG. 2) via second electrical connection 96 even though more than one of the electrical contacts 91 of lead 90 are in contact with electrical contacts 97 of second electrical connector 96, so long as each of the individual electrical contacts 91 of lead 90 are not in contact with a respective one of the electrical contacts 97.

In the example shown in FIG. 5, the different geometrical configuration of first lead 90 relative to second electrical connector 96 prevents first lead 90 from being electrically coupled to second therapy module 48, even when first lead 90 is inserted into second electrical connector 96. Accordingly, first lead 90 may be considered incompatible with second lead connector 96.

Although not shown in FIG. 5, second lead 92 may also have a geometrical configuration that prevents electrical contacts 93 of second lead 92 from electrically connecting to electrical contacts 95 of first electrical connector 94. For example, second lead 92 may have a center pin (not shown) similar to center pin 99 of first lead 90, where the center pin of second lead 92 may have a different cross-sectional shape than center pin 99. The cross-sectional shape of center pin 99 may be configured such that it may not be introduced into a bore defined by second electrical connector 96. The cross-sectional shape referred to may be a shape of the cross-section of the center pin taken in a direction substantially orthogonal to a center axis of the respective lead 90, 92. As an example, center pin 99 of first lead 90 may have a circular cross-sectional shape, while the center pin of second lead 92 may have an oblong or a rectangular cross-sectional shape.

Figure 6:
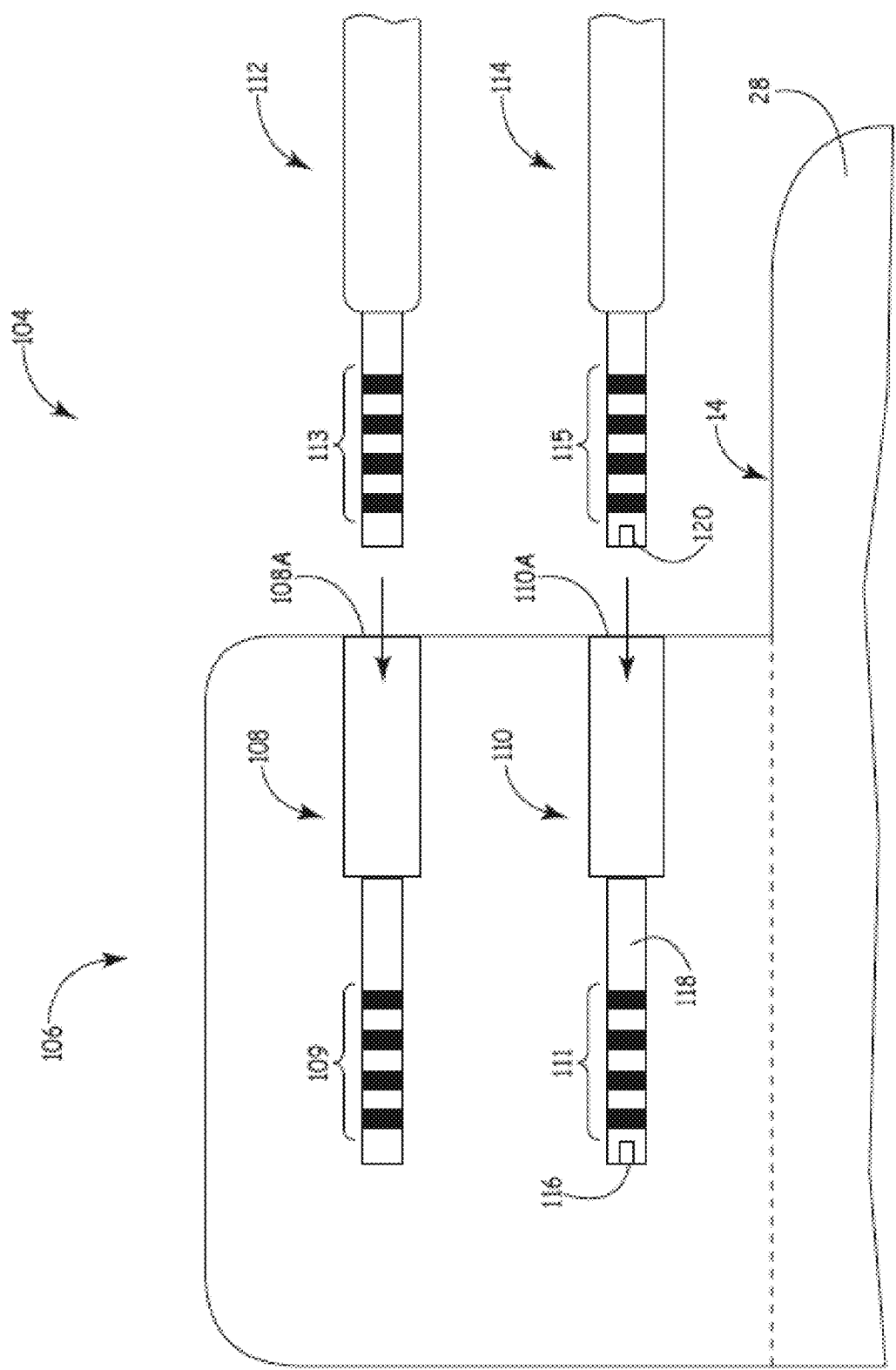
FIG. 6 is a conceptual diagram illustrating a cross-sectional view of a portion of another example therapy system that includes an electrical connector that is substantially physically incompatible with a lead.

FIG. 6 is a conceptual diagram illustrating a cross-sectional view of a portion of another example therapy system 104. Therapy system 104 comprises IMD 14, which includes lead connection assembly 106 comprising first electrical connector 108 including electrical contacts 109 that are electrically coupled to first therapy module 46 (FIG. 2) and second electrical connector 110 including electrical contacts 111 that are electrically coupled to second therapy module 48 (FIG. 2). Therapy system 104 further comprises first lead 112 including electrical contacts 113 and second lead 114 including electrical contacts 115.

First lead 112 may be introduced into first electrical connector 108 such that electrical contacts 113 of lead 112 substantially align with and contact electrical contacts 109 of electrical connector 108 in order to establish an electrical connection between first therapy module 46 and one or more stimulation and/or sensing electrodes of lead 112, which are electrically coupled to a respective one of the electrical contacts 113. In this way, first therapy module 46 may deliver at least one of pacing, cardioversion or defibrillation therapy to heart 26 of patient 12 via electrodes of first lead 112.

Second lead 114 may be introduced into second electrical connector 110 such that electrical contacts 115 of lead 114 substantially align with and contact electrical contacts 111 of electrical connector 110 in order to establish an electrical connection between second therapy module 48 (FIG. 2) and one or more stimulation and/or sensing electrodes of lead 114, which are electrically coupled to a respective one of the electrical contacts 115. In this way, second therapy module 48 may deliver electrical stimulation therapy to a nonmyocardial tissue site, e.g., a tissue site proximate a nerve and/or an extravascular tissue site, or a nonvascular cardiac tissue site within patient 12 via electrodes of second lead 114.

As with therapy system 86 of FIG. 5, the relative physical dimensions of the portions of first and second leads 112, 114 that may be received by first and second electrical connectors 108, 110, respectively, are substantially similar. Accordingly, the physical dimensions of first lead 112 may not help prevent first lead 112 from being introduced into second lead connector 110. In addition, in the example shown in FIG. 6, first and second leads 112, 114 have substantially similar electrical contact 113, 115 arrangements (e.g., spacing between the electrical contacts) and first and second electrical connectors 108, 110 have substantially similar electrical contact 109, 111 arrangements. In this way, second electrical connector 110 may be substantially electrically compatible with first lead 112.

In order to prevent first lead 112 from delivering electrical stimulation signals generated by second therapy module 48 to heart 26, second electrical connector 110 may include pin 116. Pin 116 protrudes into cavity 118 of second electrical connector 110. Second lead 114 may define bore 120 (e.g., an opening) that is configured to receive pin 116, such that when second lead 114 is introduced into opening 110A of second electrical connector 110, pin 116 may be received in bore 120. In this way, electrical contacts 111 of second electrical connector 110 substantially align with and contact a respective one of the electrical contacts 115 of second lead 114. In some examples, electrical contacts 111 may substantially fully contact a respective one of the electrical contacts 115 of second lead 114.

In therapy system 104, first lead 112 that may be positioned to deliver stimulation to heart 26, however, does not include a bore. Thus, if first lead 112 is introduced into second electrical connector 110, pin 116 may interfere with the ability of first lead 112 to be fully introduced into cavity 118 of second electrical connector 110. This may help prevent the electrical contacts 113 of first lead 112 from substantially aligning with electrical contacts 111 of second electrical connector 110. In this way, second electrical connector 110 is configured to be substantially physically incompatible with first lead 112. The physical incompatibility between second electrical connector 110 and first lead 112 may help limit or prevent first lead 112 from delivering electrical stimulation generated by second therapy module 48 to heart 26 of patient 12.

In the example shown in FIG. 6, the different geometrical configuration of first lead 112 relative to second electrical connector 110 prevents first lead 112 from being electrically coupled to second therapy module 48, even when first lead 112 is introduced into second electrical connector 110.

In some examples of therapy system 104, pin 116 of second electrical connector 110 may be conductive, and bore 120 of lead 114 may include an electrical contact that is configured to electrically contact a conductive pin 116. Processor 45 of IMD 14 (FIG. 2) may be configured to control second therapy module 48 (FIG. 2) to deliver electrical stimulation via a connected lead only if conductive pin 116 electrically connects to the electrical contact within bore 120. In this way, processor 45 may verify that the proper lead 114 is introduced into second electrical connector 110. Processor 45 of IMD 14 (FIG. 2) may determine whether pin 116 is in electrical contact with lead 90 prior to controlling therapy module 46 to deliver electrical stimulation to electrodes of lead 114. For example, processor 45 may determine an impedance of an electrical path including the center pin 116 and compare the impedance to a stored threshold value or a range of stored threshold values to determine whether the impedance indicates center pin 116 is in electrical contact with lead 114.

Although leads including four electrical contacts are shown in FIGS. 4-6, in other examples, a lead may include any suitable number of electrical contacts. In some examples, the number of electrical contacts located at a proximal portion of the lead may correspond to the number of stimulation and/or sensing electrodes at a distal portion of the lead. In addition, the electrical connectors described herein may include any suitable number of electrical contacts, which may correspond to the number of electrical contacts on a proximal portion of a lead that is introduced into the electrical connector.

Figure 7:
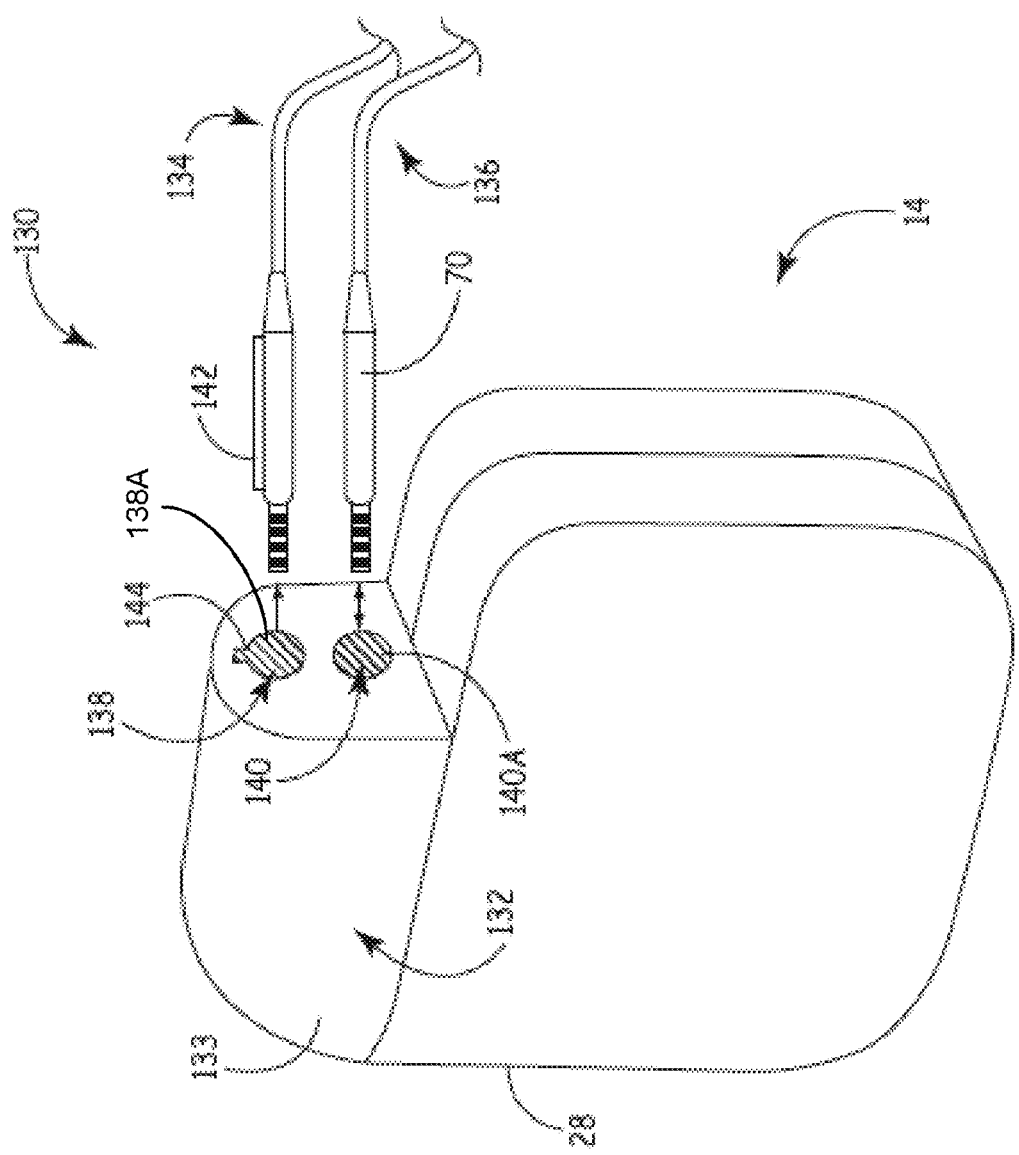
FIG. 7 is a conceptual diagram illustrating a perspective view of an example therapy system that includes an electrical connector that is substantially physically incompatible with a lead.

FIG. 7 is a conceptual diagram illustrating a perspective view of example therapy system 130, which includes IMD 14, lead connection assembly 132, first lead 134, and second lead 136. IMD 14 is described above with respect to FIGS. 1 and 2. Lead connection assembly 132 includes first electrical connector 138 that includes electrical contacts that are electrically coupled to first therapy module 46 (FIG. 2) and second electrical connector 140 that includes electrical contacts that are electrically coupled to second therapy module 48 (FIG. 2). First lead 134 may be introduced into first electrical connector 138 to electrically connect electrodes carried by first lead 134 to first therapy module 46. In addition, second lead 136 may be introduced into second electrical connector 140 in order to electrically connect electrodes carried by second lead 136 to second therapy module 48.

In the example shown in FIG. 7, second electrical connector 140 is configured to be substantially physically incompatible with first lead 134 in order to discourage a clinician from introducing first lead 134 into second electrical connector 140. While openings 138A, 140A of first and second electrical connectors 138, 140, respectively, are substantially similar in size, openings 138A, 140A may have different geometrical configurations. First lead 134 defines flange 142 and first electrical connector 138 defines a channel 144 that is configured to receive flange 142. Second electrical connector 140, on the other hand, does not define a channel that is configured to receive flange 142. As a result, first lead 134 may not be substantially fully introduced into second electrical connector 140. For example, flange 142 may interfere with the ability of lead 134 to be introduced into opening 140A of second electrical connector 140. In this way, first lead 134 may be considered to be physically incompatible with second electrical connector 140.

The physical incompatibility between second electrical connector 140 and first lead 134 may help prevent the electrodes of first lead 134 from being fully electrically connected to electrical contacts within second electrical connector 140. In some cases, some of the electrical contacts on a proximal portion of first lead 134 may contact electrical contacts of second electrical connector 140. However, this electrical connection between first lead 134 and second electrical connector 140 may be insufficient to deliver undesirable electrical stimulation to heart 26 from second therapy module 48.

In other examples, other configurations of flange 142 and channel 144 are contemplated, such as different sizes and different shapes. Flange 142 of lead 134 may comprise any suitable protrusion that extends around any suitable portion of outer perimeter of lead 134. In some examples, lead 134 may include a plurality of flange 142 with connector 138 including a plurality of channels 144 in a configuration that corresponds to the plurality of flanges of lead 134. Although in FIG. 7, only first electrical connector 138 defines channel 144 and only first lead 134 includes flange 142, in some examples, both first and second electrical connectors 138, 140, respectively, may define channels, and both leads 134, 136 may include protrusions that are configured to be received in the channels of first and second electrical connectors 138, 140. However, first and second electrical connectors 138, 140, respectively, may define different types of channels, such that second electrical connector 140 is substantially physically incompatible with the flange of first lead 134.

Alternatively or additionally, although not indicated in FIG. 7, one or more of electrical connectors 138 and 140 may possess particular magnetic properties such that second electrical connector 140 is configured to be substantially physically incompatible with first lead 134 in order to discourage a clinician from introducing first lead 134 into second electrical connector 140. For example, first electrical connector 138 may exhibit a first magnetic polarity relative opening 138A and second electrical connector 140 may exhibit a second magnetic polarity relative opening 149A that is substantially opposite of that the first magnetic polarity. In such a case, plug portion of first lead 134 may be configured to be magnetically compatible with the first magnetic polarity of first electrical connector 138 and, thus, magnetically incompatible with the second magnetic polarity of second electrical connector 140. In this manner, not only does the magnetic property of second electrical connector 140 repel attempts to introduce plug portion of first lead 134 into second electrical connector 140, the magnetic property of first electrical connector 138 may encourage connection with lead 134 and act to secure the plug portion of lead 134 within first electrical connector 138 via magnetic forces.

Similarly, in some examples, plug portion 70 of second lead 136 is configured to be magnetically compatible with the second magnetic polarity of second electrical connector 140 and, thus, magnetically incompatible with the first magnetic polarity of first electrical connector 138. In such a case, not only does the magnetic property of first electrical connector 138 repel attempts to introduce plug portion 70 of second lead 136 into first electrical connector 138, the magnetic property of second electrical connector 140 may encourage connection with lead 136 and act to secure plug 70 of lead 136 within first electrical connector 140 via magnetic forces.

Lead connection assemblies 40 (FIGS. 2-4), 88 (FIG. 5), 106 (FIG. 6), 132 (FIG. 7) described herein are configured to receive two leads. As previously indicated, in other examples, lead connection assemblies in accordance with the examples described herein may be configured to receive more than two leads, e.g., via a respective electrical connector. In examples in which a lead connection module includes more than two electrical connectors, the electrical connectors may be configured to have different geometrical configurations, electrical contact configurations, different sized openings, and/or different visual identifiers (e.g., color bands or alphanumeric identifiers). In this way, electrical connector may be configured to receive only a certain type of lead. In other examples, two of the electrical connectors may share a geometrical configurations, electrical contact configurations, and/or opening size. For example, electrical connectors used to electrically couple a respective one of the leads 18, 20, 22 (FIG. 1) to first therapy module 46 (FIG. 1) may share similar features, such that leads 18, 20, 22 may be introduced into any of the electrical connectors. In other examples, the electrical connectors of the lead connection assembly may be configured to receive a specific lead 18, 20, 22.

Figure 8:
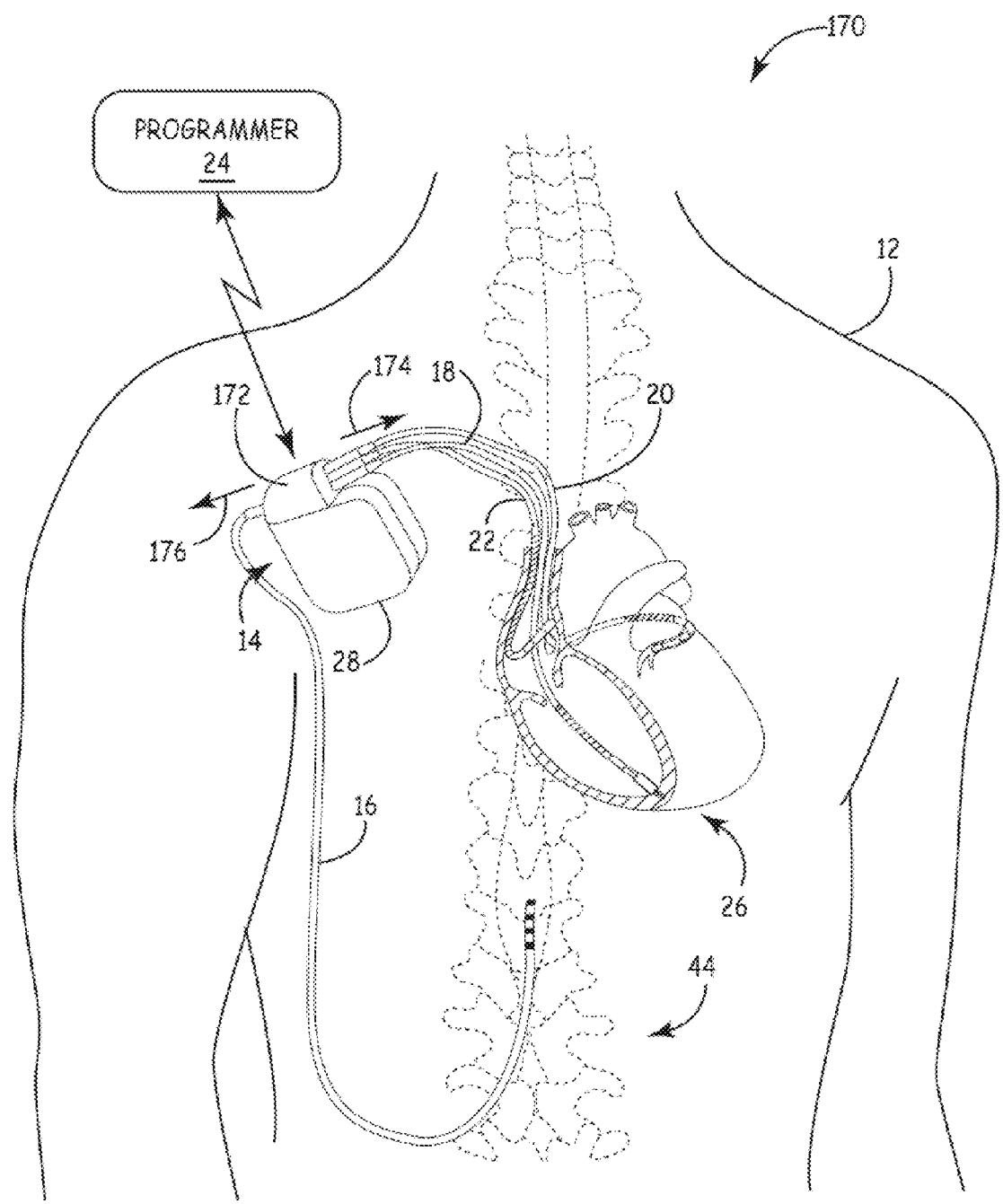
FIG. 8 is a conceptual diagram illustrating an example therapy system that includes an IMD including a lead connection assembly that includes electrical connectors defining openings for receiving leads that extend in substantially opposite directions.

FIG. 8 is a conceptual diagram illustrating an example therapy system 170 that delivers at least one of pacing, cardioversion or defibrillation therapy to heart 26, and delivers electrical stimulation to a nonmyocardial tissue site, e.g., an extravascular tissue site and/or tissue site proximate a nerve of patient 12 or a nonvascular tissue site within patient 12. System 170 may be substantially the same or similar to system 10 of FIG. 1. However, IMD 14 includes lead connection assembly 172 that is configured to accommodate different lead approaches, e.g., different angles with which leads 16, 18, 20, 22 may be mechanically coupled to lead connection assembly 172 and extend from housing 28.

Lead connection assembly 172 is configured such that leads 18, 20, 22 may extend from lead connection assembly 172 in a first direction, which is represented by arrow 174, and lead 16 may extend from lead connection assembly 172 in a second direction, which is represented by arrow 176. In particular, first direction 174 corresponds to a direction in which a proximal end of each of the leads 18, 20, 22 may be introduced into lead connection assembly 172, and second direction 176 corresponds to a direction in which a proximal end of lead 16 may be introduced in lead connection assembly 172. First direction 174 is substantially different from that of second direction 176. In the example shown in FIG. 8, first and second directions 174, 176, respectively, can be substantially opposite to each other. Lead connection assembly 172 may define openings that face in direction 174, and an opening that faces in direction 176, whereby leads 18, 20, 22 may be introduced into the openings that face in direction 174 and lead 16 may be introduced into the openings that face in direction 176.

In some examples, leads 18, 20, 22 extending from lead connection assembly 172 in first direction 174 may accommodate the implantation of electrodes of leads 18, 20, 22 within heart 26. Similarly, lead 16 extending from lead connection assembly 172 in second direction 176 may accommodate the implantation of electrodes of lead 16 proximate the respective target stimulation site for the delivery of electrical stimulation generated by second therapy module 48 (FIG. 2). For example, first direction 174 may correspond to the relative direction of the path that leads 18, 20, 22 may follow from IMD 14 to heart 26 when implanted in patient 12, and second direction 176 may correspond to the relative direction of the path that lead 16 may follow from lead connection assembly 172 to spinal cord 44 when implanted in patient 12.

In some examples, lead connection assembly 172 that accommodates the extension of leads from housing 28 in different directions, e.g., via openings that face in different directions, for accommodating the different target stimulation sites of therapy system 10 may minimize the length of a lead implanted in patient 12 to reach from IMD 14 the target stimulation location, such as, e.g., spinal cord 44 and/or heart 26. This may help decrease the overall intensity of stimulation required to stimulate tissue by decreasing the impedance of the electrical path between the therapy modules 46, 48 of IMD 14 and the target stimulation site. Decreasing the intensity of stimulation required to stimulate tissue may help conserve power source 50 (FIG. 2) of IMD 14, which may extend the useful life of IMD 14. An intensity of stimulation may be a function of, for example, a current or voltage amplitude of stimulation signal, the frequency of the stimulation signal, the shape of the stimulation signal, the duty cycle of the stimulation signal, or the electrode combination used to deliver the stimulation signal.

Lead connection assembly 172 that accommodates the extension of leads from housing 28 in different directions, e.g., via openings that face in different directions, for accommodating the different target stimulation sites of therapy system 10 may also help maintain the integrity of leads 16, 18, 20, 22 by decreasing the stresses imposed on leads 16, 18, 20, 22 attributable to traversing a path including one or more sharp turns. That is, lead connection assembly 172 may help decrease the number of sharp turns or other awkward configurations of one or more of leads 16, 18, 20 or 22 when the one or more leads traverse from IMD 14 to a target tissue site within patient 12. This may help decrease the stresses on leads 16, 18, 20, 22, which may help maintain the integrity of conductors within the respective lead and/or the insulation of the respective lead that separates the electrical conductors from each other and/or from tissue of patient 12. This may also simplify the lead connection process and also reduce the length and/or amount of leads located within the pocket (e.g., a subcutaneous pocket) related to the implant. For example, the extension of leads from different direction may assist a physician in identifying the proper connector corresponding to particular type of lead, thereby encouraging connection of a lead into the particular electrical connector and discouraging connecting the lead into an improper connector. Such a configuration may decrease the likelihood of inadvertent connection of a lead to the improper electrical connector, and increase the efficiency of the device implantation procedure.

Figure 9:
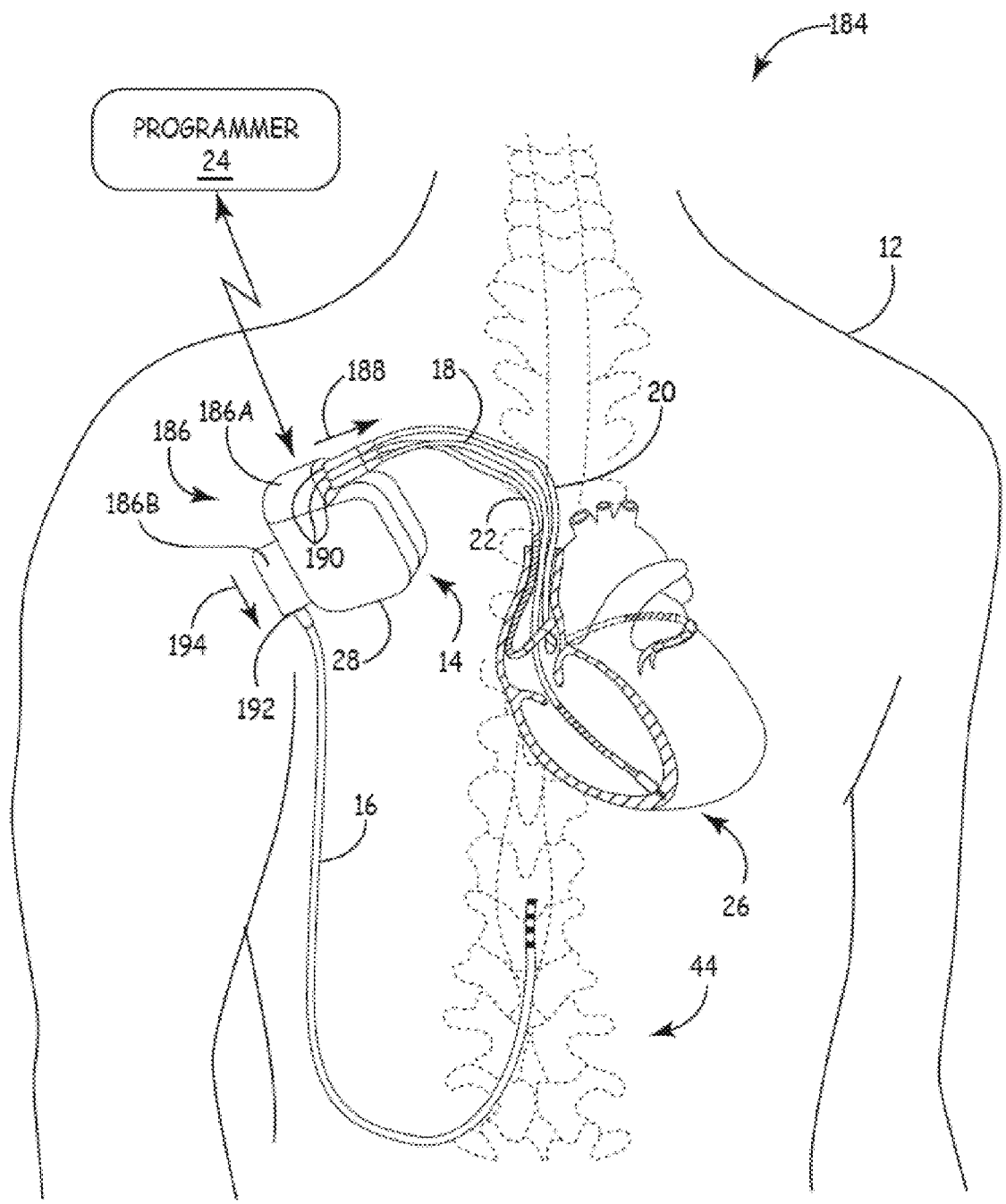
FIG. 9 is conceptual diagram illustrating an example therapy system that includes an IMD including a lead connection assembly that includes electrical connectors defining openings for receiving leads that extend from the IMD housing in substantially different directions.

FIG. 9 is conceptual diagram illustrating another example therapy system 184 that may be used to deliver at least one of pacing, cardioversion or defibrillation therapy to heart 26, and deliver electrical stimulation to a nonmyocardial tissue site, e.g., an extravascular tissue site and/or tissue site proximate a nerve of patient 12 or a nonvascular cardiac tissue site. System 184 may be substantially similar to system 170 of FIG. 9. However, IMD 14 is connected to multiple lead connection assemblies 186A, 186B, rather than a single lead connection assembly 172. First electrical connector 186A connects electrodes of leads 18, 20, 22 to IMD 14 to first therapy module 46 (FIG. 2) of IMD 14. Second electrical connector 186B connects electrodes of lead 16 to second therapy module 48 (FIG. 2) of IMD 14. In the example of FIG. 9, electrical connectors 186A and 186B each define individual lead connection assemblies that are separate from one another.

As shown in FIG. 9, first electrical connector 186A is configured such that leads 18, 20, 22 extend from housing 28 of IMD 14 in a first direction 188. For example, first electrical connector 186A may define openings 190 through which leads 18, 20, 22 may be introduced into lead connection assembly 186. Second connection assembly 186B is configured such that lead 16 extends from housing of IMD 14 in a second direction 194 that is different than first direction 188. For example, second electrical connector 186B may define opening 192 through which lead 16 may be introduced into lead connection assembly 186. Opening 192 may face a different direction than openings 190 of first electrical connector 186A.

In the example of FIG. 9, first direction 188 may be a direction of a physical path through tissue between IMD 14 and a target stimulation site for the pacing, cardioversion and/or defibrillation signals delivered via electrodes of leads 18, 20, 22. Second direction 194 may correspond to a direction of a physical path through tissue between IMD 14 and a target stimulation site for electrical stimulation generated by second therapy module 48 (FIG. 2) via electrodes of lead 16.

In some examples, directions 188, 194 may be substantially orthogonal to each other, although other relative directions with which leads 18, 20, 22 and lead 16 may extend from housing 28 of IMD 14 are also contemplated.

As discussed with respect to FIG. 8, using lead connection assembly 186A and 186B permits leads to extend therefrom in different directions may help increase the ease with which therapy system 184 may be implanted within patient 12, despite the fact that leads 18, 20, 22 and lead 16 may deliver stimulation to substantially different tissue sites within patient 12. In addition, lead connection assembly 186A and 186B may help minimize the length of one or more of the leads 16, 18, 20, 22 by enabling a clinician to implant therapy system 10 such that at least one of the leads 16, 18, 20, 22 extends from IMD 14 to a target tissue site via a more direct route. Further, just as with lead connection assembly 172 (FIG. 8), lead connection assembly 186A and 186B may help decrease the stresses imposed on at least one of the leads 16, 18, 20, 22 by decreasing the turns that the lead may take in the traversal from IMD 14 to a target tissue site. Moreover, the physical separation of lead connection assemblies 186A and 186B may minimize electromagnetic interference between lead 16 and leads 18, 20, 22 and/or the electrical circuits to which lead 16 and lead 18, 20, 22 electrically connect.

Figure 10:
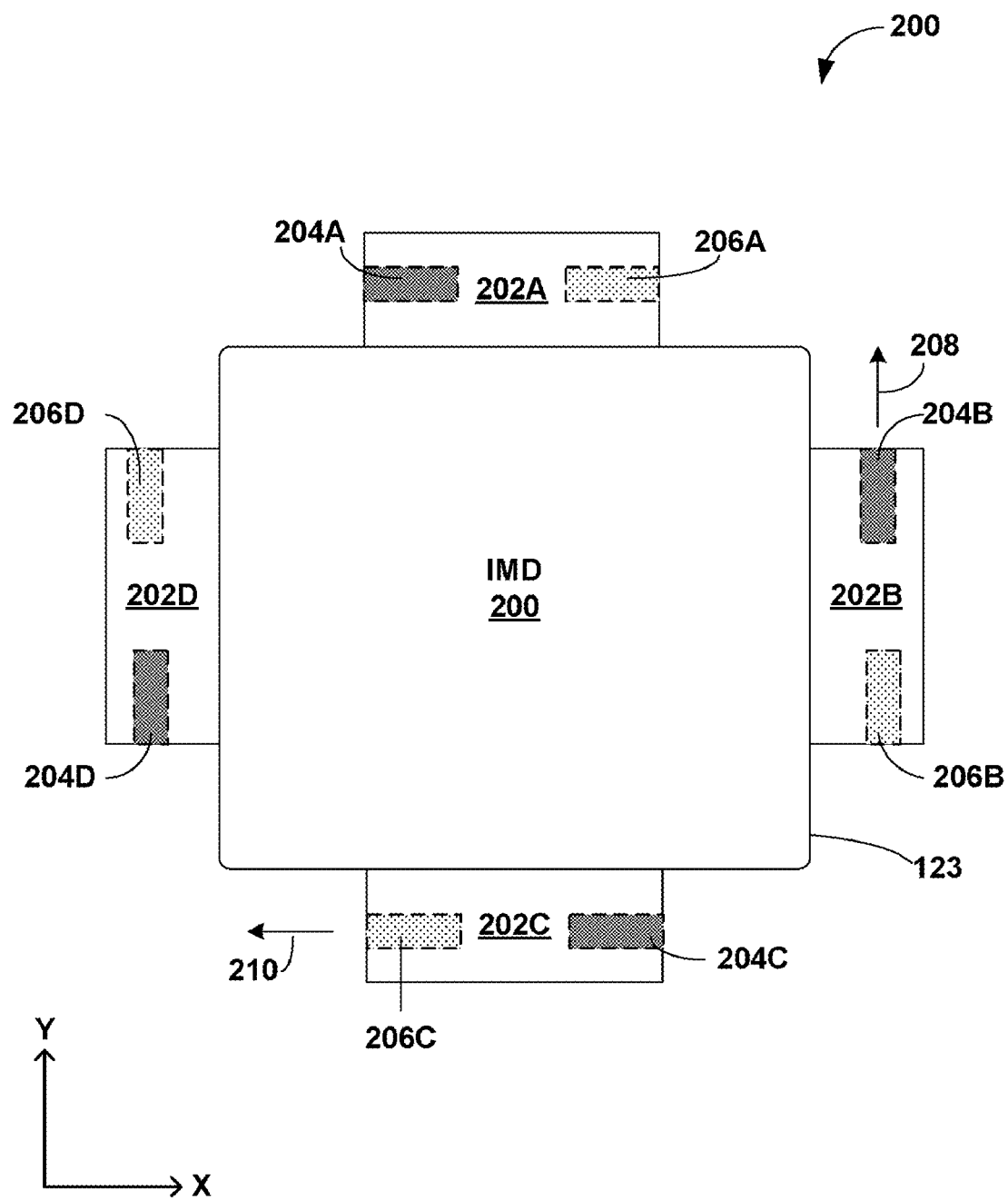
FIG. 10 is a conceptual diagram illustrating an example IMD comprising a lead connection assembly with a plurality of electrical connectors.

FIG. 10 is a conceptual diagram illustrating example IMD 200 and lead connection assemblies 202A, 202B, 202C, 202D (collectively "lead connection assemblies 202"). Each lead connection assembly 202A-202D includes a first electrical connector 204A-204D, respectively, and a second electrical connector 206A-206D, respectively. First electrical connectors 204A-204D and second electrical connectors 206A-206D may be receptacle type electrical connectors configured to receive a proximal portion of one or more implantable leads (not shown). For example, each of the first electrical connectors 204A-204D may be substantially similar to first electrical connector 54 of lead connection assembly 40 (FIG. 2) or first electrical connector 94 of lead connection assembly 88 (FIG. 5), and each of the second electrical connectors 206A-206D may be substantially similar to second electrical connector 56 of lead connection assembly 40 (FIG. 2) or second electrical connector 96 of lead connection assembly 88 (FIG. 5).

In some examples, each first electrical connector 204A-206D may be configured to electrically couple one or more leads to a first therapy module, such as, e.g., first therapy module 46, to deliver a first type of electrical stimulation to patient 12 (e.g., at least one of a pacing, cardioversion or defibrillation therapy). In addition, in some examples, each second electrical connector 206A-206D may be configured to electrically couple one or more leads to a second therapy module, such as, e.g., second therapy module 48, to deliver a second type of electrical stimulation to patient 12. In other examples, first electrical connectors 204A-204D and second electrical connectors 206A-D may be electrically coupled to the same therapy module within IMD 200.

Lead connection assemblies 202 each mechanically couple to leads (either directly or indirectly via a lead extension), such that the leads extend from an outer housing 123 of IMD 200 in different directions. In the example shown in FIG. 10, lead connection assemblies 202A-202D each define openings that face in substantially opposite directions. For example, lead connection assemblies 202A, 202C each define openings that face in substantially positive direction along an x-axis (orthogonal x-y axes are shown in FIG. 10) and a substantially negative direction along the x-axis. In the example shown in FIG. 10, lead connection assemblies 202B, 202D each define openings that face in substantially positive direction along a y-axis and a substantially negative direction along the y-axis.

One or more leads may be coupled to any one or more lead connection assemblies 202A-202D in order to deliver therapy from IMD 200 to patient 12. Moreover, both electrical connectors 204A-204D, 206A-206D of each lead connection assembly 202 need not be used at the same time (e.g., need not receive a respective lead at the same time). For example, a first lead may be introduced into electrical connector 204B of lead connection assembly 202B to electrically couple the first lead to the first therapy module of IMD 200, such that the first lead extends from housing 123 of IMD 200 in a first direction 208, e.g., approximately the positive y-axis direction. At the same time, a second lead may be introduced into electrical connector 206C of lead connection assembly 202C to electrically couple the second lead to the second therapy module of IMD 200, such that the second lead extends from housing 123 in a second direction 210, e.g., approximately the negative x-axis direction.

IMD 200 including lead connection assemblies 202 that each define lead-receiving openings that face in different directions may support a greater number of IMD 200 implant sites within patient 12 and/or therapy delivery to a greater number of target stimulation sites within patient 12 compared to an IMD including a single lead connection assembly that includes one or more openings facing in a common direction. During implantation of a therapy system including IMD 200 and one or more leads in patient 12, a clinician may adapt the therapy system to different implantation sites within patient 12, and/or different target stimulation sites within patient 12 by electrically coupling the one or more leads to the lead connection assembly 202 that best accommodates the desired path between IMD 200 and the target tissue site. For example, the clinician may couple the lead to the lead connection assembly 202 that provides the shortest path between IMD 200 and the target tissue site, or the less tortuous path (e.g., with fewer turns). In this way, IMD 200 may be adaptable to different types of therapy systems or different patient anatomies.

IMD 200 may be implanted into patient 12 without specific regard to the orientation of housing 123 within patient 12, while still allowing for implantable leads to be received by lead connection assemblies 202 according to four distinct directions for each the first therapy module and second therapy module. In this manner, IMD 200 may be useful for more than one implantation configuration within a patient 12. For example, regardless of whether IMD 200 is implanted in the lower back or upper chest of patient 12, both a first and second lead may be received by at least one of a first electrical connector 204A-204D and at least one of a second electrical connect 206A-206D, respectively, to electrically couple first lead to first therapy module 46 in anyone of the four directions described.

In some examples, some of the electrical connectors 204A-204D and 206A-206D may not be mated with a lead. In such examples, a protective member may be inserted into or seal the lead-receiving openings defined by one or more of the unmated electrical connectors 204A-204D and 206A-206D in order to isolate the electrical components of the respective connectors from the internal environment of patient 12, as well as protect components of IMD 200 from fluid or other particle ingress. In this manner, the internal components IMD 200 may be adequately protected within patient 12 despite the presence of one or more unmated electrical connectors.

Figure 12A:
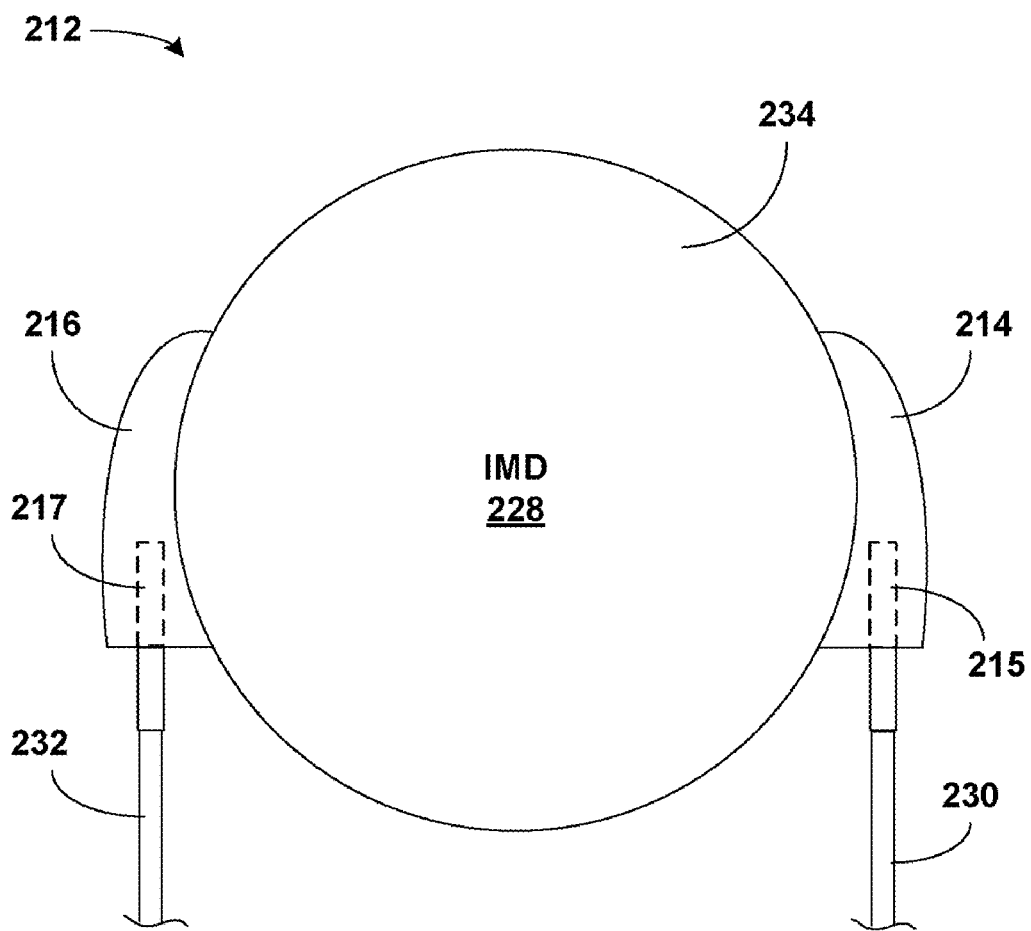
FIGS. 12A and 12B are conceptual diagrams illustrating a portion of an example therapy system including an example IMD and two example lead connection assemblies from plan views, respectively.
Figure 12B:
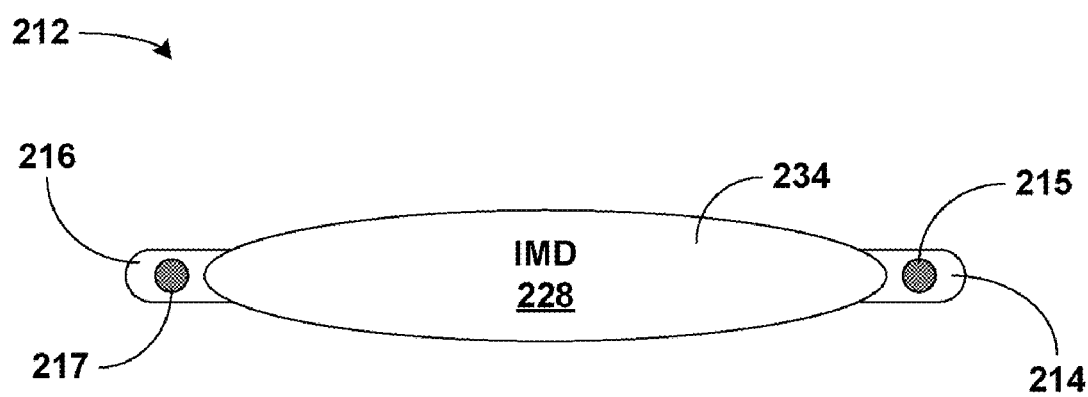
Figure 13:
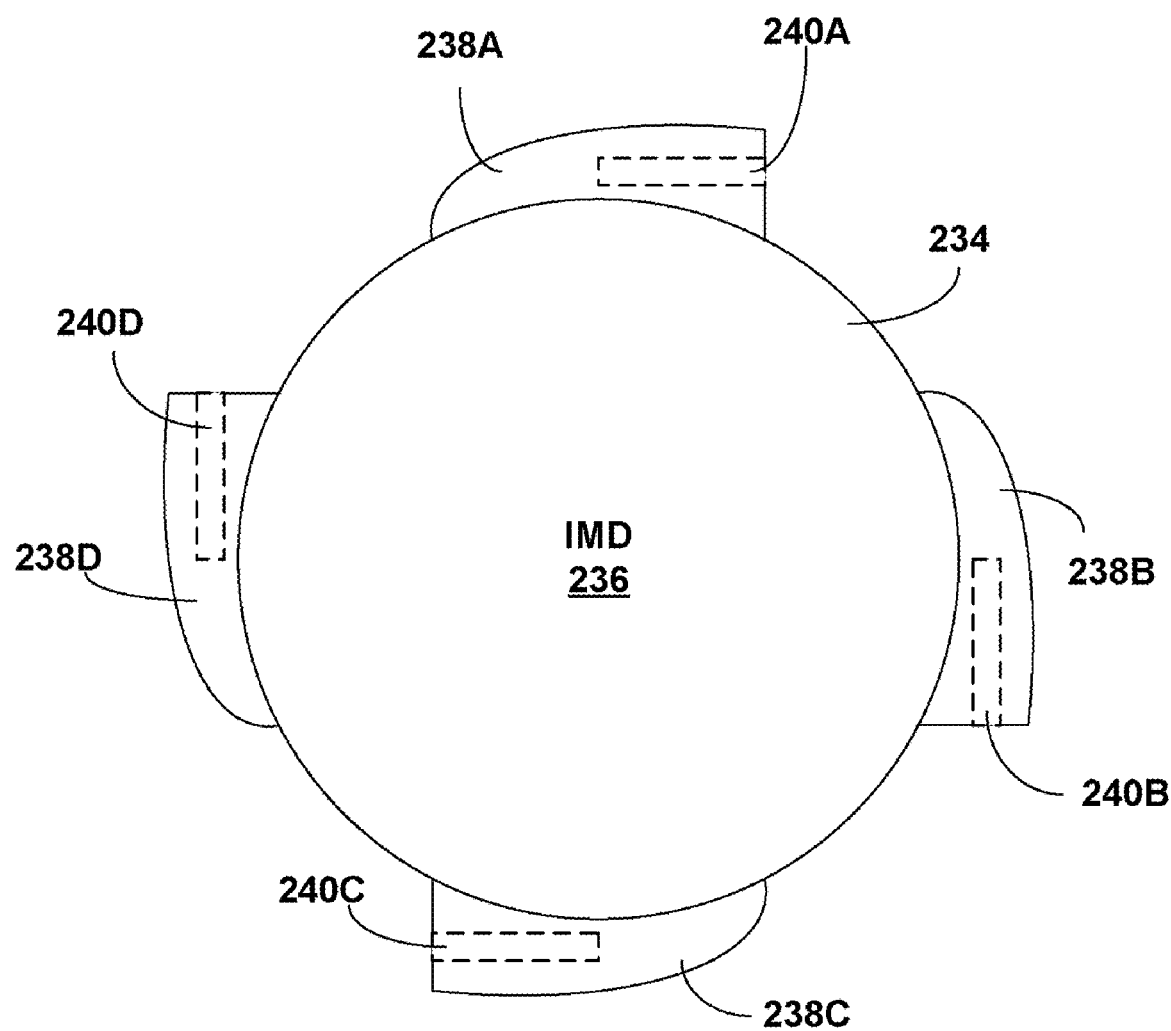
FIG. 13 is a conceptual diagram illustrating an example IMD including a plurality of lead connection assemblies.

The relative shape of the outer housing of IMD 200 is not limited to the substantially square shape shown in FIG. 10. In some examples, IMD 200 may be configured in other suitable shapes having any suitable number of sides on which electrical connection assemblies may be positioned, such as, e.g., in a substantially triangular shape defining three sides. In such an example, IMD 200 may include three electrical connection assemblies rather than the four electrical connection assemblies 202A-202D shown in FIG. 10, with each of the three sides including an electrical connection assembly. As another, IMD 200 may be configured in a substantially circular or disk shape. For example, a disk-shaped housing may define a round housing with top and bottom major surfaces that are substantially flat. In these and other examples, IMD 200 may include one or more electrical connection assemblies at any location around the outer perimeter of the IMD 200. Examples of IMDs having an outer housing configured in a circular or disk shape are illustrated in FIGS. 12A, 12B, and 13. Moreover, a housing of IMD 200 or any other IMD described herein may comprise any suitable outer surface, such as a nonplanar outer surface, which may be less irritating to tissue of patient 12.

As mentioned previously, in some aspects, the disclosure relates to therapy systems including an IMD with a plurality of lead connection assemblies, which may also be referred to as headers or connector blocks, rather than a single lead connection assembly. The plurality of lead connection assemblies may be configured to mechanically and electrically connect one or more leads to the same or different therapy module within a common IMD, e.g., for delivery of electrical stimulation therapy to a patient. For example, in the example shown in FIG. 9, therapy system 184 includes IMD 14 and first and second lead connection assemblies 186A and 186B. First lead connection assembly 186A mechanically and electrically connects leads 18, 20 and 22 to IMD 14, e.g., for delivery of pacing, cardioversion and/or defibrillation signals to heart 26 via one or more electrodes of leads 18, 20 and 22. Second lead connection assembly 186B mechanically and electrically connects lead 16 to IMD 14, e.g., for delivery of electrical stimulation signal to tissue proximate to spinal cord 44 via one or more electrodes of lead 16.

As another example, IMD 200 illustrated in FIG. 10 has four lead connection assemblies 202A-202D, each of which includes a first electrical connector 204A-204D, respectively, and a second electrical connector 206A-206D, respectively, for connecting one or more leads to IMD 200. As described above, each first electrical connector 204A-206D may be configured to electrically couple one or more leads to a first therapy module, such as, e.g., first therapy module 46 (FIG. 2), to deliver a first type of electrical stimulation to patient 12 (e.g., at least one of a pacing, cardioversion or defibrillation therapy), and each second electrical connector 206A-206D may be configured to electrically couple one or more leads to a second therapy module, such as, e.g., second therapy module 48 (FIG. 2), to deliver a second type of electrical stimulation to patient 12. In such an example, each individual lead connection assembly includes both electrical connectors for electrical coupling one or more leads to the first therapy module and electrical coupling one or more leads to the second therapy module. In other examples, some or all of the individual lead connection assembly may include one or more electrical connectors to couple one or more leads to either the first therapy module or second therapy module but not to both the first and second therapy modules.

Furthermore, while electrical connection assemblies 204 of FIG. 10 are described with regard to electrically coupling one or more leads to first and second therapy modules of an IMD, in some examples, a plurality of lead connection assemblies may connect one or more leads to a single therapy module of an IMD. For example, one or more leads may be electrically coupled to a single therapy module of an IMD, e.g., a therapy module configured for one or more of pacing, cardioversion or defibrillation therapy, via two or more lead connection assemblies positioned adjacent to different portions of the IMD housing. When position adjacent to a portion of the IMD housing, a lead connection assembly may be mechanically attached to the housing of IMD 200 or integral with the housing 123.

Figure 11:
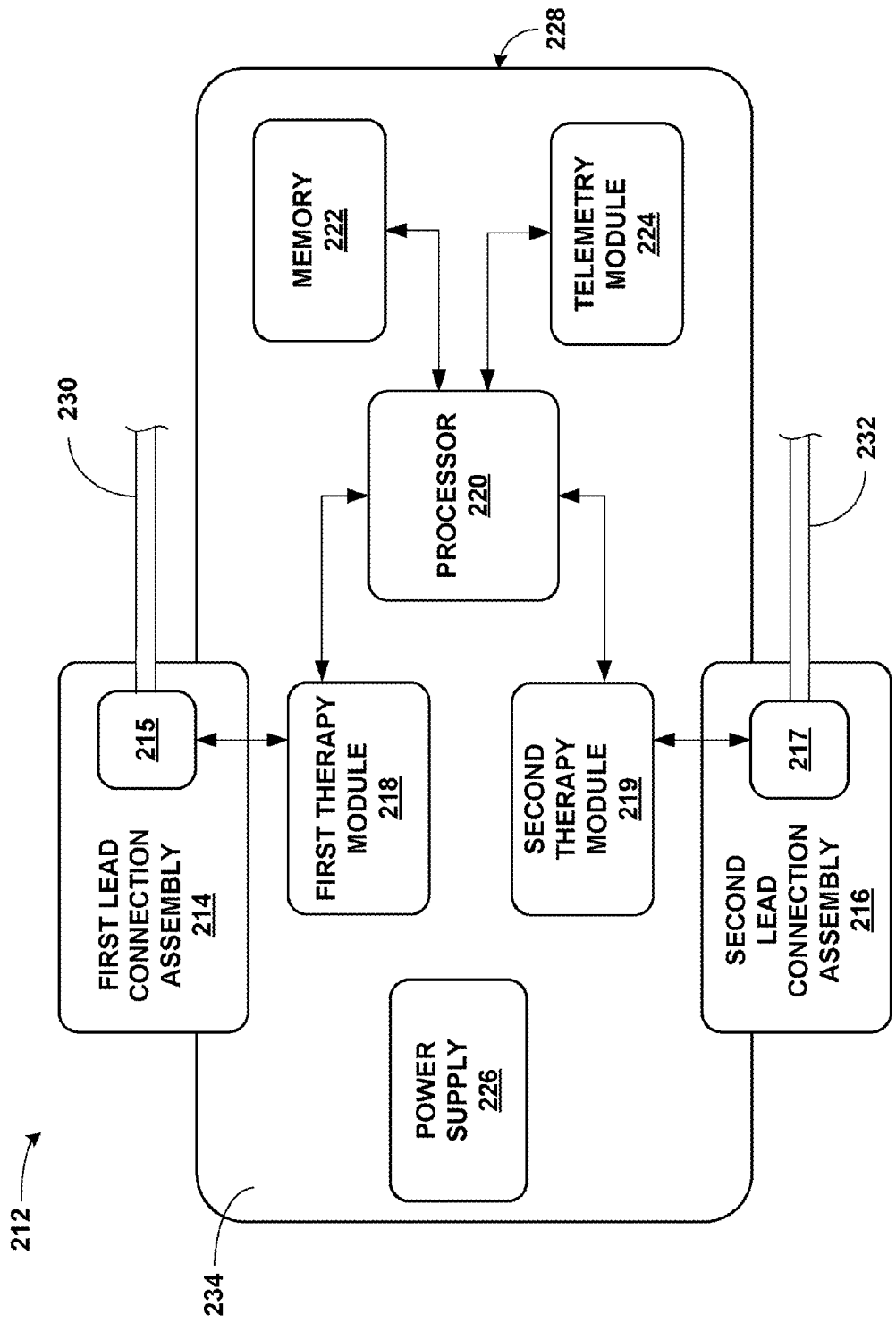
FIG. 11 is a functional block diagram illustrating an example therapy system including an example IMD and two example lead connection assemblies.

FIG. 11 is a functional block diagram illustrating an example therapy system 212. Therapy system 212 includes IMD 228, first lead connection assembly 214, second lead connection assembly 216, lead 230, and lead 232. Lead 230 is mechanically connected to IMD 228 via first lead connection assembly 214 and lead 232 is mechanically connected to IMD 228 via second lead connection assembly 216, which is physically separate from first lead connection assembly 214. Although FIG. 11 illustrates each of first and second lead connection assemblies 214 and 216 as being configured to receive a single lead, lead connection assemblies in accordance with this disclosure may be configured to receive any suitable number of leads, such as one, two, three, four or more.

As shown in FIG. 11, IMD 228 includes first therapy module 218, second therapy module 219, processor 220, memory 222, telemetry module 224 and power supply 226. In some aspects, IMD 228 may be substantially the same or similar to that of IMD 14, which has been described previously. For example, processor 220, memory 222, telemetry module 224 and power supply 226 may be substantially the same or similar to that of processor 45, memory 49, telemetry module 52, and power supply 50, respectively, of IMD 14 (FIG. 2).

First and second lead connection assemblies 214 and 216 mechanically couple lead 230 and lead 232, respectively, to IMD 228, and electrically couple the electrodes of leads 230 and lead 232 to first therapy module 218 and second therapy module 219, respectively, of IMD 228. For example, first lead connection assembly 214 includes first electrical connector 215 that is configured to receive lead 230. In some examples, the housing of first lead connection assembly 214 may at least partially enclose first electrical connector 215, e.g., the housing of first lead connection assembly 214 may enclose substantially all of first electrical connector 215. When lead 230 is properly connected to first electrical connector 215, electrical stimulation generated by first therapy module 218 is selectively conducted from first therapy module 218 to heart 26 of patient 12 (FIG. 1) or any other target tissue of patient 12 via conductors and electrodes of lead 230 (under the control of processor 220).

Similarly, second lead connection assembly 216 may include second electrical connector 217 that is configured to receive lead 232. In some examples, the housing of second lead connection assembly 216 (which may be separate from that of the housing of first lead connection assembly 214) may at least partially enclose second electrical connector 217, e.g., the housing of second lead connection assembly 216 may enclose substantially all of second electrical connector 217. When lead 232 is properly connected to second electrical connector 217 of second lead connection assembly 216, electrical stimulation generated by second therapy module 219 is selectively conducted from second therapy module 219 to heart 26, spinal cord 44, (FIG. 1) or any other target tissue of patient 12 via conductors and electrodes of lead 230. In this respect, first lead connection assembly 214 is configured to electrically couple lead 230 to first therapy module 218, and second lead connection assembly 216 is configured to electrically couple lead 232 to second therapy module 219.

First therapy module 218 of IMD 228 may include a signal generator that is configured to generate stimulation signals, e.g., electrical stimulation signals, associated with a first stimulation therapy which may be delivered to patient 12 via one or more electrodes of lead 230. Second therapy module 219 of IMD 228 may include a signal generator that is configured to generate stimulation signals, e.g., electrical stimulation signals, associated with a second stimulation therapy other than that of the first stimulation therapy, which may be delivered to patient 12 via one or more electrodes of lead 232.

First therapy module 218 may configured to generate and deliver stimulation therapy that is different than the simulation therapy generated and delivered by second therapy module 219. For example, first therapy module 218 may include electronic circuitry configured to generate electrical stimulation signals of a first stimulation therapy, and second therapy module 219 may include electronic circuitry configured to generate electrical signals of a second stimulation therapy. The electronic stimulation circuitry configured to generate the electrical signals of the second therapy may be separate from that of the electronic stimulation circuitry configured to generate the electrical signals of the first therapy. For example, first therapy module 218 may include electronic circuitry used to generate the first therapy stimulation signals that is different from the electronic circuitry of the second therapy module 219 used generate the second therapy stimulation signals. In some examples, IMD 228 may include a single die stack that includes both the electronic circuitry of first therapy module 218 and the electronic circuitry of the second therapy module 218. In some examples, the electronic circuitry of the first and second therapy modules 218, 219 may be partitioned from one another to provide for separate generation of the first therapy signals and second therapy signals, respectively.

Example types of stimulation therapy include deep brain stimulation (DBS), spinal cord stimulation (SCS), peripheral nerve stimulation (PNS), peripheral nerve field stimulation (PNFS), gastrointestinal tract stimulation, urinary tract stimulation, and the like. In some examples, first therapy module 218 may be configured to generate stimulation signals for pacing, cardioversion, and/or defibrillation stimulation therapy for delivery to heart 26 (FIG. 1) of patient 12 via lead 230, while second therapy module 219 may be configured to generate stimulation signals for neurostimulation therapy for delivery to patient 12 via lead 232. The different type of stimulation therapy may be configured to treat one or more patient conditions associated with the respective therapy. As such, in some examples, first therapy module 218 and second therapy module 219 may be configured to generated stimulation therapy for treating different patient conditions, at least to the extent that the respective therapy module 218, 219 generate stimulation signals for stimulation therapies that are different from one another. In some examples, the electrical stimulation signals generated by first therapy module 218 may be configured to be delivered to a first tissue site of patient 12 while the electrical stimulation signals generated by second therapy module 219 may be configured to be delivered to second tissue site of patient 12 that is different than the first tissue site.

In some examples, therapy module 218 may be substantially the same or similar to first therapy module 46 (FIG. 2). For example, first therapy module 218 may generate and deliver at least one of pacing, cardioversion or defibrillation therapy to heart 26 of patient 12 via lead 230. If first therapy module 218 is configured to generate and deliver defibrillation pulses to heart 26 of patient 12, first therapy module 218 may include a high voltage charge circuit and a high voltage output circuit. If first therapy module 218 is configured to generate and deliver pacing pulses to heart 26, processor 220 may include pacer timing and control module, which may be embodied as hardware, firmware, software, or any combination thereof. The pacer timing and control module may comprise a dedicated hardware circuit, such as an ASIC, separate from other processor components, such as a microprocessor, or a software module executed by a component of processor 220, which may be a microprocessor or ASIC. The pacer timing and control module may be used by processor 220 to time the delivery of pacing pulses to heart 26.

Although not shown in FIG. 11, similar to that of IMD 14 (FIG. 1), IMD 228 may also include a sensing module that monitors signals from at least one of the electrodes of leads 230, 232 and/or one or more electrodes defined by or coupled to outer housing 234 in order to monitor electrical activity of heart 26, e.g., via an EGM signal, or other patient tissue site. In some examples, the sensing module may include one or more sensing channels, each of which may comprise an amplifier. Under the control of processor 220, the switch module of the sensing module may couple the outputs from the selected electrodes to one of the sensing channels. The sensed electrical activity of heart 26 may be used to control the timing of the delivery of pacing, cardioversion or defibrillation shocks by first therapy module 218. For example, processor 220 may employ any suitable arrhythmia detection methodologies in order to detect an arrhythmia based on electrical cardiac signals sensed by the sensing module, and the detection of an arrhythmia may be used to control the delivery of defibrillation shocks by first therapy module 218, e.g., to attempt to terminate the detected arrhythmia.

In some examples, second therapy module 219 may be configured substantially similar to second therapy module 48 (FIG. 2) of IMD 14. For example, second therapy module 219 may generate and deliver electrical stimulation therapy (e.g., neurostimulation) to a nonmyocardial tissue site (e.g., a tissue site proximate a nerve and/or an extravascular tissue site not proximate a nerve) or a nonvascular cardiac tissue site (e.g., a cardiac fat pad) via electrodes of lead 232. In examples in which IMD 228 is substantially similar to that of IMD 14 (FIG. 2), (e.g., first therapy module 218 being substantially similar to that of first therapy module 46 and second therapy module 219 being substantially similar to that of second therapy module 48) IMD 228 may generate and deliver both cardiac and neurostimulation therapy to patient 12 via lead 230 and lead 232, respectively.

Depending on the particular type of therapy generated by first and second therapy modules 218 and 219, lead 230 and lead 232 may be substantially similar to that of any one or more of leads 16, 18, 20 and 22 (FIG. 1) or a lead extension electrically and mechanically coupled to one or more of leads 16, 18, 20 and 22 (FIG. 1). For example, if first therapy module 218 is configured to generate and deliver at least one of pacing, cardioversion or defibrillation therapy to heart 26 of patient, lead 230 may be substantially similar to that of one or more of leads 18, 20, 22 (FIG. 1). Similarly, if second therapy module 219 is configured to generate and deliver electrical stimulation therapy (e.g., neurostimulation) to a nonmyocardial tissue site or a nonvascular cardiac tissue site, then lead 232 may be substantially similar to that of lead 16 (FIG. 1).

In some examples, lead 230 and/or lead 232 may be associated with one or more sensing devices that monitor physiological parameters of patient 12, such as, e.g., blood pressure, muscle activity, and the like. In such a case, first lead connection assembly 214 and/or second lead connection assembly 216 may electrically couple lead 230 and/or lead 232, respectively, to a sensing module (not shown) that is configured to analyze the sensor signals to monitor physiological parameter values of patient 12. In some examples, first lead connection assembly 214 may electrically couple lead 230 to a sensing module, alternatively or in addition to, first therapy module 218, while second lead connection assembly 216 may electrically couple lead 232 to second therapy module 219. In this manner, IMD 228 may sense one or more physiological parameters of patient 12 via first lead connection assembly 218 and delivery electrical stimulation therapy to patient 12 via second lead connection assembly 219.

First electrical connector 215 and second electrical connector 217 may be substantially the same or similar to the electrical connectors previously described with above, e.g., as described with regard to first and second electrical connectors 54 and 56 (FIGS. 2-4). In some examples, first electrical connector 215 may be incompatible with lead 232 (e.g., based on size, shape, electrical contact arrangement, and/or visible identifiers), and/or second electrical connector 217 may be incompatible with lead 230. Alternatively, each of first and second electrical connectors 215 and 217 may be compatible with each of leads 230 and 232.

First electrical connector 215 and/or second electrical connector 217 may include multiple electrical connectors for connecting multiple leads to first therapy module 218 and second therapy module 219, respectively. For example, first lead connection assembly 214 may include multiple electrical connectors, each of which may be used to electrically couple a lead, such as lead 230, to first therapy module 218. In such an example, the multiple electrical connectors may be electrical connector of the same type, e.g., electrical connectors configured to mate with substantially the same type of lead-side connector. In other examples, first lead connection assembly 214 may include multiple electrical connectors of different types, e.g., electrical connectors configured to mate with different types of lead-side connectors. The electrical connector types can have, for example, different diameters, different electrical contact arrangements, and/or can be unipolar or bipolar. Example types of electrical connector types may include, but are not limited to, electrical connectors conforming to published standards IS-1 (defined by International Standard ISO 5841.3:1992; having approximately 3.2 millimeter diameter, and used, e.g., to deliver relatively low voltage pacing signals and to sense electrophysiological signals), DF-1 (defined by International Standard ISO 11318: 1993, and, e.g., used to deliver relatively high voltage defibrillation shocks), IS-4, and DF-4, non-standard formats for cardiac therapy leads, non-standard sensor leads, and electrical connectors for connecting neuromodulation stimulation leads of various configurations, e.g., quadrapolar or octopolar connectors.

Figure 14:
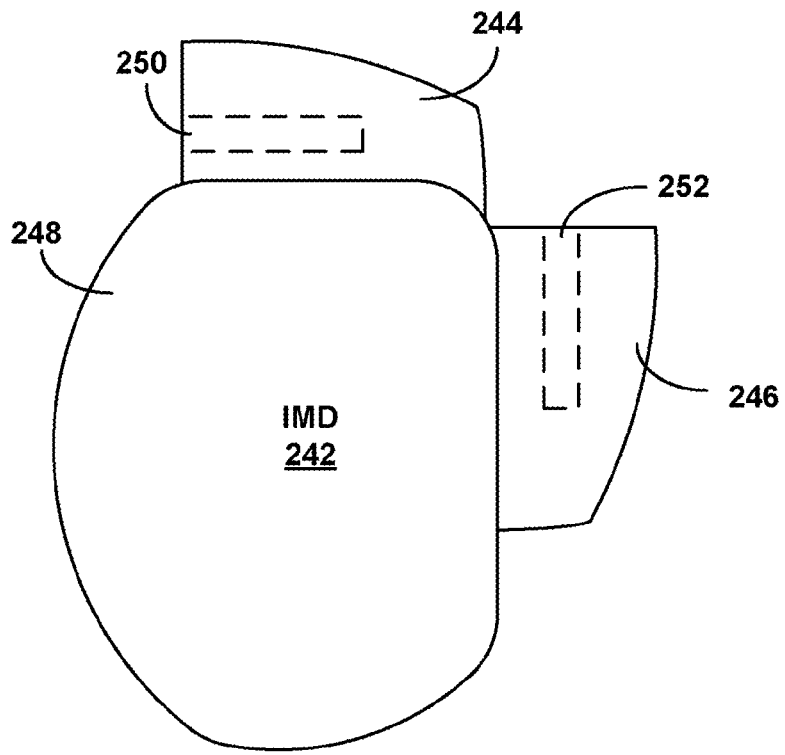
FIG. 14 is a conceptual diagram illustrating another example IMD including two lead connection assemblies.
Figure 15:
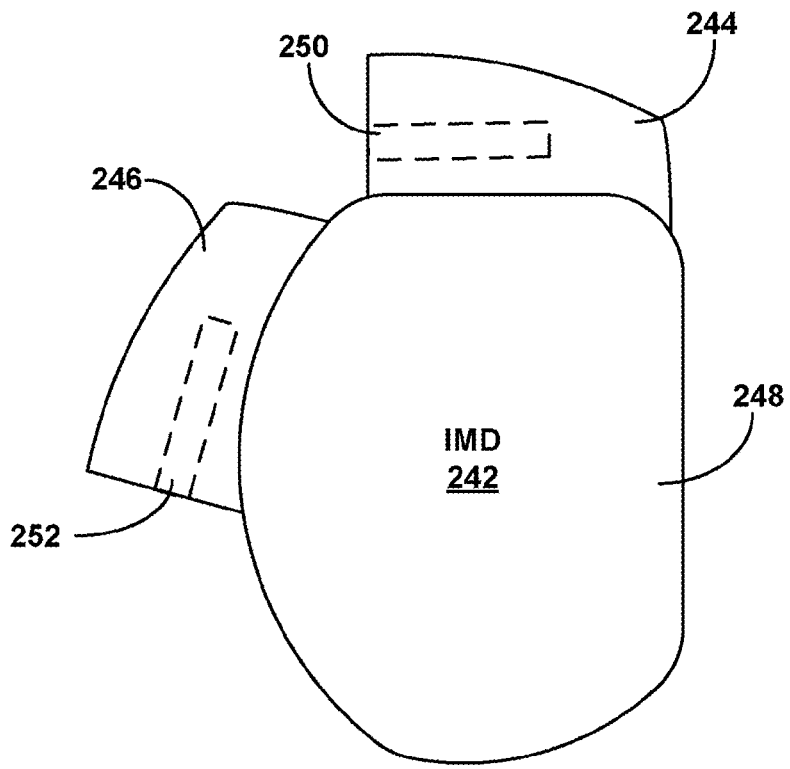
FIG. 15 is a conceptual diagram illustrating another example IMD including two lead connection assemblies.

As shown in FIG. 11, first lead connection assembly 214 and second lead connection assembly 216 may be separate from one another on housing 234 of IMD 228. For example, first lead connection assembly 214 and second lead connection assembly 216 may be physically separate from each other and positioned at different parts of housing 234. As will be described further below, for example, FIGS. 12A and 12B illustrate IMD 228 having first lead connection assembly 214 and second lead connection assembly 216 physically separate from one another and positioned at different parts of housing 234 (e.g., at substantially opposite radial positions on the periphery of disk-shaped housing 234). As another example, FIG. 13 illustrates IMD 236 having four separate lead connection assemblies 238A-D positioned at different parts of housing 234 of IMD 236 (e.g., distributed radially around the perimeter of housing 234. As another example, FIGS. 14 and 15 illustrate IMD 242 having first lead connection assembly 244 and second lead connection assembly 246 physically separate from one another and positioned at different of housing 234.

First lead connection assembly 214 may be configured to connect to one or more feedthroughs (not shown) on hermetically sealed housing 234 to form a conductive path from first therapy module 218 to first electrical connector 215, and second lead connection assembly 216 may be configured to connect to one or more feedthroughs (not shown) also on housing 234 that are separate from those corresponding to first lead connection assembly 214 to form a conductive path from second therapy module 219 to second electrical connector 217. The feedthroughs may allow housing 234 of IMD 228 to maintain a hermetic seal while also allowing stimulation energy generated within housing 234 (e.g., via first therapy module 218 and second therapy module 219) to be conducted across housing 234 to electrical connector 215, 217 of first and second connection assemblies 214, 216, respectively.

In some examples, each of first and second lead connection assemblies 214, 216 may form distinct physical structures (e.g., lead connection assembly housings) mechanically attached to the outer surface of housing 234. The physically structure of each lead connection assembly 214, 216 may at least partially contain first and second electrically connectors 215, 217, respectively, although the lead connection assemblies may not be hermetically sealed (although the housing of each of first and second lead connection assemblies 214, 216 may provide suitable fluid sealing and electrical coupling for components of the assembly, e.g., electrical connector 215, 217). The connection between the one or more feedthroughs of each therapy module 218, 219 and electrical connectors 215, 217 of each lead connection assembly 218, 219 may be covered by the physical structure of the respective lead connection assembly when attached to IMD housing 234. For example, the housing of first lead connection assembly 214 may cover the one or more feedthroughs associated with first therapy module 215 when attached to housing 234 in a manner that allows first electrical connector 215 to be electrically coupled to first therapy module 218. In such a configuration, first lead connection assembly 214 may not cover the feedthroughs associated with second therapy module 219. Rather, the housing of second lead connection assembly 216 may cover such feedthroughs when attached to housing 234 in a manner that allows second electrical connector 217 to be electrically coupled to second therapy module 219. As will be described below, first lead connection assembly 214 may be attached (or integrally formed) on housing 234 of IMD 228 at or adjacent to separate portions of housing 234. For example, first lead connection assembly 214 and second lead connection assembly 216 may be positioned or attached on separate sides housing 234. Each lead connection assembly 214 and 216 may be mechanically attached to housing 234 of IMD 228 or integral with housing 234 of IMD 228.

Outer housing 234 of IMD 228 substantially encloses components of IMD 228, such as first therapy module 218, second therapy module 219, processor 220, memory 222, telemetry module 224, and power supply 226. In the example shown in FIG. 11, first and second lead connection assemblies 214, 216 are positioned at different locations along outer housing 234. In such a configuration of first and second lead connection assemblies 214, 216, the proximal end of lead 230 (or lead extension) mechanically couples to IMD 228 (via the electrical connector 215 of first lead connection assembly 214) at a different physical location on housing 234 than lead 232.

In the example shown of therapy system 212 shown in FIG. 11, a plurality of lead connection assemblies 214, 216 are separated from each other and distributed about outer housing 234 of IMD 228. As described below, compared to therapy systems in which a single lead connection assembly mechanically and electrically couples to a plurality of leads at the same location of the outer housing of an IMD, the distributed lead connection assembly configuration of therapy system 212 may increase the ease with which a clinician may implant therapy system 212 in patient 12 and/or address tissue in growth issues associated with implanted therapy systems. Moreover, the physical separation of first and second lead connection assemblies 214 and 216 may minimize electromagnetic interference between leads 230, 232 and/or the electrical circuits to which leads 230, 232 electrically connect For example, the physical separation between the leads 230, 232 and the electrical connection between leads 230, 232 and therapy modules 218, 219, respectively, achieved by the separate lead connection assemblies 214, 216 may increase the resistance between conductors of lead 230 and 232. In some examples, the physical separation of connection assemblies 214, 216 may minimize or reduce cross-coupling (or "crosstalk") between one or more channels, e.g., stimulation channels and/or sensing channels, associated with conductors of the lead(s) coupled to first therapy module 218 via first lead connection assembly 214 and one or more channels associated with conductors of the lead(s) coupled to second therapy module 219 via second lead connection assembly 215. For examples, by physically separating connection assemblies 214, 216, leakage current or electrical signals from one channel associated one or more leads coupled via first lead connection assembly 214 does not significantly affect the function (e.g., sensing or stimulation) of another channel associated with one or more leads coupled via second lead connection assembly 215, and vice versa.

In some examples, first lead connection assembly 214 and second lead connection assembly 216 may be configured such that lead 230 may be mechanically coupled to IMD 228 and electrically coupled to either first therapy module 218 or second therapy module 219 via first and second lead connection assembly 214 and 216, respectively. For example, first electrical connector 215 of first lead connection assembly 214 may be substantially the same as that of second electrical connector 217 of second lead connection assembly 216. As such, lead 230 may be connected to IMD 228 either via first lead connection assembly 214 or via second lead connection assembly 216. Similarly, in some examples, lead 232 may also be mechanically and electrically connected to IMD 228 either via first lead connection assembly 214 or via second lead connection assembly 216. However, in such cases, attention may be required to ensure lead 230 and 232 are electrically coupled to the desired therapy module as first therapy module 218 and second therapy module 219 may be configured to generated different stimulation therapies.

In examples in which one or both of lead connection assemblies 214, 216 are configured to receive multiple leads, e.g., examples in which first and/or second lead connection assembly 218, 218 has multiple electrical connectors, processor 220 may automatically or semi-automatically identify when a lead is received in the respective electrical connector. When a lead is received in the electrical connector of an electrical connection assembly, processor 220 may identify the lead connection assembly and/or the particular electrical connector of the lead connection assembly as "active." An identification of the "activated" lead connection assemblies 214, 216 and/or electrical connectors 215, 217 that have received leads may be useful for controlling first and second therapy modules 218, 219. For example, in order for processor 220 to control the delivery of therapy to patient 12 by first and second therapy modules 218, 219, processor 220 may need to initially determine which electrical paths are "active" for delivery of electrical stimulation signals.

In some examples, processor 220 may also distinguish between multiple lead connected to the same lead connection assembly. For example, processor 220 may recognize that lead 230, connected to first therapy module 218 via lead connection assembly, is configured to be or expected to be implanted in left ventricle 36 of heart 26 (FIG. 1), such as, e.g., lead 20 (FIG. 1), and that a second lead, also connected to first therapy module 218 via first lead connection assembly 218, is configured to be or expected to be located in the right ventricle 32 of heart 26 (FIG. 1), such as, e.g., lead 18 (FIG. 1). By identifying the types of leads connected to the lead connection assemblies 214, 216, processor 220 may control the electrical path to which different types of electrical stimulation therapy are delivered to patient 12 for the respective therapy modules 218, 219. Additionally or alternatively, a user, such as a clinician may communicate such information to IMD 228 via programmer 24 after therapy system 10 is implanted in patient 12 (FIG. 1).

As another example, in a configuration in which first therapy module 218 generates pacing stimulation and second therapy module 219 generates defibrillation stimulation therapy signals, processor 220 may control first therapy module 218 to deliver the pacing signals using first lead connection assembly 214 and control second therapy module 219 to deliver the defibrillation signals using second lead connection assembly 216. In such an example, one or more electrodes on lead 230 may deliver pacing stimulation signals to patient 12, and one or more electrodes on lead 232 may deliver defibrillation signals to patient 12. As defibrillation signals may have a relatively high voltage compared to that of the pacing signals, IMD 228 may be configured such that first lead connection assembly 214 is used to deliver high voltage stimulation signals and second lead connection assembly 216 is used to deliver low voltage stimulation signals. In this way, therapy system 212 including separate lead connection assemblies 214, 216 distributed about an outer perimeter of housing 234 helps physically separate the relatively high voltage and relatively low voltage electrical stimulation delivery paths. This may help reduce any electromagnetic interference and/or cross-coupling that may be generated between the relatively high voltage and relatively low voltage electrical stimulation delivery paths. In some examples, first lead connection assembly 214 may be used to deliver electrical stimulation signals within a range of voltage that is different than the voltage range of electrical stimulation delivered via second lead connection assembly 216. For example, first therapy module 218 may generate and deliver electrical stimulation having voltages greater than 20 volts, greater than 100 volts, or greater than 600 volts. In some examples, first therapy module 218 may deliver electrical stimulation having voltages between approximately 20 volts and approximately 1000 volts, such as, e.g., between approximately 750 volts and approximately 800 volts, between approximately 600 volts to approximately 775 volts, between approximately 100 volts and approximately 200 volts, or between approximately 90 volts and approximately 775 volts. Second therapy module 219 may generate and deliver electrical stimulation having voltages less than approximately 20 volts, such as, e.g., between zero volts and approximately 10 volts, such as, between zero volts and approximately 8 volts, or zero volts and approximately 5 volts, or between approximately 0.5 volts and approximately 10 volts, such as, between approximately 0.5 volts and approximately 8 volts, between approximately 0.5 volts and approximately 5 volts, between approximately 1 volt and approximately 5 volts, or between approximately 6 volts and approximately 8 volts.

In configurations in which IMD 228 delivers one type of stimulation therapy generated by first therapy module 218 to patient 12 using first lead connection assembly 214, e.g., cardiac therapy signals, and delivers another type of therapy generated by second therapy module 219 to patient 12 using second lead connection assembly 216, e.g., neurostimulation therapy signals, first lead connection assembly 214 and second lead connection assembly 216 can be configured to deliver a single type electrical stimulation therapy or multiple types of stimulation therapy. For example, if IMD 228 only delivers neurostimulation therapy signals using second lead connection assembly 216, second lead connection assembly 216 may be configured the same or substantially similar to that of a lead connection assembly of an IMD that only delivers neurostimulation therapy. Similarly, if IMD 228 only delivers cardiac therapy signals, e.g., one or more of pacing, cardioversion, and defibrillation signals, using first lead connection assembly 214, then first lead connection assembly 214 may be configured the same or substantially similar to that of a lead connection assembly of an IMD that only delivers cardiac rhythm management therapy. Thus, if IMD 228 is configured to deliver both neurostimulation and cardiac rhythm management therapy, lead connection assemblies 214, 216 do not necessarily have to be configured to couple to both cardiac leads (e.g., leads 18, 20, 22 in FIG. 1) and a neurostimulation lead (e.g., lead 16 in FIG. 1). For example, first and second lead connection assemblies 214, 216 may be unique to the respective type of therapy delivered via each assembly 214, 216.

FIGS. 12A and 12B are conceptual diagrams illustrating a portion of example therapy system 212 including IMD 228 with first lead connection assembly 214 and second lead connection assembly 216 from plan views. First lead connection assembly 214 includes first electrical connector 215 and second lead connection assembly 216 includes second electrical connector 217.

Therapy system 212 also includes lead 230 and lead 232 (not shown in FIG. 12B), which are shown in FIG. 12A with proximal ends inserted into first electrical connector 215 and second electrical connector 217, respectively. As shown, first and second electrical connectors 215 and 217 may be receptacle type electrical connectors configured to receive a proximate portion of implantable leads 230 and 232, respectively. When properly inserted in electrical connectors 215 and 217, leads 230 and 232 are electrically and mechanically coupled to IMD 212 via lead connection assemblies 214 and 216, respectively. IMD 212, first lead connection assembly 214, second lead connection assembly 216, lead 230 and lead 232 have been described above with respect to FIG. 11.

In the example illustrated in FIGS. 12A and 12B, housing 234 of IMD 228 defines a disk-shaped member, e.g., housing 234 may have a circular shape (as shown in FIG. 12A) with a substantially flat or slightly curved upper and lower major surfaces (as shown in FIG. 12B). In some examples, housing 234 may have a diameter between approximately 30 millimeters to approximately 90 millimeters. The thickness of housing 234 may be between approximately 4 millimeters to approximately 16 millimeters. In some examples, housing 234 may have a diameter between approximately 0.5 inches to approximately 2 inches. In some examples, the diameter of housing 234 may be between approximately 1 to 6 inches, such as, e.g., approximately 1.5 inches to approximately 3 inches, and the thickness of housing 234 may be between approximately 0.25 and approximately 2 inches, such as, e.g., approximately 0.4 to 0.75 inches. In other examples, IMD 228 may have other dimensions and may have a shape other than that shown in FIGS. 12A and 12B, e.g., IMD 228 may be triangular rather than circular. Other dimensions besides those described above are contemplated. In general, the dimensions of IMD 228 provide a device that is suitable for implantation within patient 12.

First and second lead connection assemblies 214 and 216 are located on the periphery of IMD 228, and extend from the disk-shaped housing in a low-profile manner, e.g., such that the respective assemblies protrude a minimal amount from the outer perimeter of housing 234. Additionally, first lead connection assembly 214 and second lead connection assembly 216 are located adjacent to separate portions of housing 234 of IMD 228. In the example shown in FIG. 12, first lead connection assembly 214 is positioned substantially across a major surface of housing 234 from second lead connection assembly 216. Other relative positions of first and second lead connection assemblies 214, 216 are contemplated. In some examples, the low-profile of lead connection assemblies 214, 216 and shape of housing 234 may provide for patient comfort when implanted. The shape of IMD 228 may also provide for ease of handling for a clinician during an implantation procedure, e.g., when inserting IMD 228 in a subcutaneous pocket.

Due to the distribution of lead connection assemblies 214, 216 along an outer perimeter of housing 234, the location or point at which the proximal end of lead 230 mechanically couples to first electrical connector 215, e.g., where lead 230 is inserted into the opening of first electrical connector 215, is separate from the location or point at which the proximal end of lead 232 mechanically couples to second electrical connector 217. While first and second lead connection assemblies 214, 216 are configured such that leads 230 and 232 extend from the respective lead connection assemblies 214, 216 and from housing 234 in substantially the same direction, in other examples, first and second lead connection assemblies 214, 216 may be configured such that leads 230 and 232 extend from the respective lead connection assemblies and from housing 234 in different directions, e.g., as shown in FIG. 9.

Therapy system 212 that distributes lead connection assemblies 214, 216 about an outer perimeter of housing 234 may help facilitate the connection of leads 230, 232 to IMD 228. For example, separating the locations at which the proximal ends of leads 230 and 232 connect to IMD 228 via first and second lead connection assemblies 214 and 216, respectively, may help provide better access (e.g., visual and physical access) to the electrical connectors 215, 217, respectively, during a process in which therapy system 212 is implanted in patient 12. In this way, a clinician may more easily connect leads 230 and 232 to the corresponding lead connection assemblies during implantation of therapy system 212 in patient 12 compared to a configuration in which an IMD includes a single lead connection assembly with all of the electrical connectors for connecting multiple leads to the IMD. Depending on the orientation that IMD is implanted in the patient, it may be relatively difficult for the clinician to access the electrical connectors when the electrical connectors are grouped together at the same physical location on the IMD. Access to the electrical connectors of an IMD including a single lead connection assembly may also be difficult if the openings for the electrical connectors are on the same face of the lead connection assembly (e.g., as shown in FIG. 1 and FIG. 3) because of the relatively small size of the electrical connectors and the space limitations for accessing the electrical connectors.

When an IMD is configured such that two or more leads associated with the therapy system are connected via multiple electrical connectors on a single lead connection assembly, the electrical connectors may be positioned in relatively close proximity to one another. Accordingly, once a clinician connects the first lead (or lead extension) to the corresponding electrical connector of the lead connection assembly during the procedure to implant the therapy system in a patient, the proximal end of the connected lead may present a visual and/or physical obstruction that interferes with the connection of the remaining leads to remaining electrical connectors. The obstruction associated with connected leads is generally exacerbated as number of leads connected to the lead connection block increases. In some examples, having separate lead connection assemblies for different therapy modules within the housing of an IMD may facilitate a multi-stage, e.g., two-stage, implant process. For example, in a case when an IMD may deliver neurostimulation therapy to a patient via a first lead connection assembly and cardiac stimulation therapy to the patient via a second lead connection assembly, different clinicians may be charged with implanting the leads corresponding to the respective therapies. By separating the lead connection assemblies and lead connectors for coupling leads to each therapy module, a first clinician may be able to implant cardiac leads followed by a second clinician to implant the one or more leads for neurostimulation therapy.

Therapy systems including multiple lead connection assemblies distributed about an IMD housing may help improve the visual and/or physical access to electrical connectors. As shown in FIGS. 12A and 12B, proximal end of lead 230 connects to first electrical connector 215 of lead connection assembly 214 at a substantially different physical location (relative to housing 234 of IMD 228) than the connection location of the proximal end of lead 232 to second electrical connector 217 of lead connection assembly 216. In this manner, during implantation of therapy system 212 in patient 12, the visual and/or physical obstruction presented by lead 230 during the connection of lead 232 to IMD 228, and vice versa, is reduced compared to an example in which lead 230 and lead 232 are connected to the same lead connection assembly.

As described above, in some examples, at least one of the lead connection assemblies 214, 216 can include multiple electrical connectors for connecting to a respective one of a plurality of leads. In such examples, the distribution and physical separation of lead connection assemblies 214, 216 from each other relative to housing 234 may still facilitate easier visual and physical access to the electrical connectors. In general, the distribution and physical separation of lead connection assemblies 214, 216 from each other helps simplify each lead connection location. This in turn may help provide better visual and physical access to the electrical connectors of the lead connection assemblies compared to examples in which all of the electrical connectors are grouped together at a common lead connection assembly.

After implantation of therapy system 212 in patient 12, tissue ingrowth may form around therapy system 212, such as the location at which leads 230, 232 connect to IMD 228. While tissue ingrowth may be useful for fixing a position of therapy system 212 within patient 12, the more fibrous tissue that forms around therapy system 212, the more difficult it may be to explant therapy system 212 from patient 12. As a result, it may be desirable to limit the amount of tissue ingrowth. Tissue ingrowth around therapy system 212 may be facilitated by textured surfaces or other surfaces having abnormal profiles. Accordingly, tissue ingrowth may be relatively prevalent around the interface between leads 230, 232 and lead connection assemblies 214, 216, respectively.

In examples in which lead connection locations are dispersed around an outer perimeter of housing 234 of IMD 228 (via multiple lead connection assemblies), less tissue ingrowth may form around the interface between leads 230, 232 and lead connection assemblies 214, 216 compared to an example therapy system in which leads 230, 232 connect to an IMD via a single connection header. For example, separating the connection points of leads 230, 232 to IMD 228 may help reduce the surface protrusions at the interfaces between leads 230, 232 and lead connection assemblies 214, 216, which may help reduce the tissue ingrowth at the interfaces. In examples in which all the leads of a therapy system mechanically connect to an IMD via a single connection header, the concentration of the leads in a relatively small space, which may cause more stress to tissue, which may further facilitate tissue ingrowth. In contrast, in the example therapy system 212 shown in FIGS. 12A and 12B, as well as other therapy systems that include spatially distributed lead connection assemblies, physically separating the lead connection points may help reduce the stress to tissue and minimize tissue ingrowth at the lead-device interface. In examples, separating lead connection locations by providing separate lead connection assemblies 214, 216 may reduce the stress, e.g., mechanical stress, on leads connected to assemblies 214, 216 by having fewer lead in proximity to one another.

Examples of IMD 228 are not limited to those in which first and second lead connection assemblies 214 and 216 each include only a single electrical connector. For example, in some examples, first lead connection assembly 214 and/or second lead connection assembly 216 may include a plurality of lead connectors configured to connect to one or more leads. As shown in FIGS. 12A, 12B, and 13, the use of multiple lead connection assemblies with IMD 228 may allow for the multiple lead connection locations to be dispersed around the housing 234 of IMD 228 rather than being grouped together at a singular portion of housing 234 as in the case in which an IMD has a single lead connection assembly. In general, as the number of lead connection assemblies increases, the ratio of lead connectors per lead connection assemblies decreases, and lead connections may be more dispersed around housing 234 of IMD 228. As discussed above, reducing the lead density at a connection point to housing 234 of IMD 228 may help reduce visual and physical obstructions to electrical connectors, and may also help reduce tissue ingrowth at the interface between the leads (or lead extensions) and lead connection assemblies.

FIG. 13 is a conceptual diagram illustrating an example IMD 236 including four lead connection assemblies 238A-238D (collectively "lead connection assemblies 238"). Each lead connection assembly 238A-238D includes an electrical connector 240A-240D (collectively "electrical connectors 240"), respectively. IMD 236 may be substantially the same or similar to IMD 228 (FIG. 11). However, unlike IMD 228, IMD 236 includes four lead connection assemblies 238 rather than two lead connection assemblies 214 and 216. Lead connection assemblies 240 are located on the periphery of housing 234, which defines a disk-shape substantially similar to that of IMD 228 (FIGS. 12A and 12B). Lead connection assemblies 240 extend from housing 234 in a low-profile manner.

Electrical connectors 240 may each be receptacle type electrical connectors configured to receive a proximal portion of one or more implantable leads (not shown). Electrical connectors 240 may each be configured to electrically couple one or more implantable leads (not shown) to either first therapy module 218 or second therapy module 219 of IMD 236. In particular, when the proximal portion of an implantable lead, such as lead 232, is properly inserted into any of electrical connectors 240, the implantable lead may deliver therapy signal(s) generated by one of first therapy module 218 or second therapy module 219 to patient 12 (FIG. 1) via one or more electrodes. In some examples, the same number (e.g., half) of lead connection assemblies 238 may be configured to electrically couple one or more leads to first therapy module 218 (FIG. 11) as that configured to electrically couple one or more leads to second therapy module 219 (FIG. 11). In other examples, a different number of lead connection assemblies 238 (e.g., 3 to 1) may be configured to electrically couple one or more leads to first therapy module 218 (FIG. 11) compared to that configured to electrically couple one or more leads to second therapy module 219 (FIG. 11). Multiple lead connection assemblies 238 may be electrically coupled to the same therapy module, (e.g., either first therapy module 218 or second therapy module 219).

Lead connection assemblies 238 are each configured to receive a lead from a different approach, which is defined by the lead-receiving opening corresponding to electrical connectors 240. That is, when a lead is introduced into each of the lead connection assemblies 238, the lead extends from an outer housing 234 of IMD 236 in a different direction. Accordingly, similar to that of IMD 200 (FIG. 10), IMD 236 includes multiple lead connection assemblies 238 that define lead-receiving openings that face in different directions.

In some examples, the different directions in which the lead-receiving openings of each of lead connection assemblies 238 face correspond to different implant sites within patient 12 and/or different target stimulation sites within patient 12. In other examples, despite including electrical connectors that define openings that face in different directions, IMD 236 may be configured to deliver therapy to a single implant site within patient 12. For example, IMD 236 may be configured to deliver one or more of pacing, cardioversion, or defibrillation signals to heart 26 of patient 12 (FIG. 1). In such an example, the distal portions of the implantable leads connected more than one lead connection assemblies 238 on housing 234 of IMD 236 may all be located within in or near heart 26 of patient 12. However, the distribution of lead connection assemblies 238 around an outer perimeter of housing 234 of IMD 236 helps disperse the lead-receiving openings on housing 234. Separating the lead-receiving openings may provide better access (e.g., less obstructed access) to the electrical connectors, thereby allowing a clinician to more easily connect multiple leads to a single IMD 236 via lead connectors 240 compared to an IMD with multiple lead-receiving openings, e.g., lead connector openings, in a single lead connection assembly.

In some examples, prior to or after connecting a lead to a lead connection assembly of IMD 236, a clinician creates strain relief loops around housing 234 with lead 236. The configuration of lead connection assemblies 238 around housing 234 may help facilitate the looping of multiple leads around housing 234 in an organized manner. In particular, electrical connectors 240 of lead connection assemblies 238 are arranged such that when leads are introduced in electrical connectors 240, the leads naturally loop around housing 234 in the same rotational direction (e.g., clockwise as shown in FIG. 13 or counterclockwise in other examples). The rotational direction, e.g., clockwise or counter-clockwise, of the lead-receiving openings defined by electrical connectors 240 may correspond to the direction that a clinician may coil the excess proximal portion of an implantable lead during implantation of IMD 236 and the leads in patient 12. In some examples, a reduction in subcutaneous pocket bulk thickness may be realized from the natural looping of lead around housing 234, thereby reducing potential for pocket erosion.

In some examples, some of electrical connectors 240 may not be mated with a lead. In such examples, a protective member may be inserted into or seal the one or more of the unmated electrical connectors 240 in order to isolate the electrical components of the respective connectors from the internal environment of patient 12, as well as protect components of IMD 236 from fluid or other particle ingress. In this manner, the internal components IMD 236 may be adequately protected within patient 12 despite the presence of one or more unmated electrical connectors 240.

FIGS. 14 and 15 are conceptual diagrams illustrating an example IMD 242 including first lead connection assembly 244 and second lead connection assembly 246. IMD may be substantially the same or similar to IMD 228 (FIG. 11). First lead connection assembly 244 and second lead connection 246 are located on the periphery of housing 248. First lead connection assembly 244 includes first electrical connector 250 and second lead connection assembly 246 includes second electrical connector 252. First and second electrical connectors 250, 252 may each be receptacle type connectors configured to receive the proximal portion of one or more implantable leads (not shown).

As shown in FIG. 14, first lead connection assembly 244 may be positioned on housing 248 of IMD 242 to provide additional mechanical support for the proximal portion of a lead inserted within second electrical connector 252 of second lead connection assembly 246. For example, the proximal portion of a lead extending out of electrical connector 252 may be prevented from bending in the direction of first lead connection assembly 244 e.g., due to engagement with the housing of first lead connection assembly 244 by virtue of the position of first lead connection assembly 244 relative to second lead connection assembly 246 on housing 248. In some examples, the housing of first lead connection assembly 244 may be shaped to guide the lead away from housing 248. In some examples, the housing of first lead connection assembly 244 may be configured such that a portion of a lead connected to second electrical connector 252 of second lead connection assembly 246 may be affixed, e.g., via a mechanical fastener, to the housing of first lead connection assembly 244 to provide additional mechanical support for the proximal portion of a lead connected to second electrical connector 252, as well as functioning to secure the proximal end of the lead within second electrical connector 252.

In a similar manner, in the configuration shown in FIG. 15, second lead connection assembly 246 may be positioned on housing 248 of IMD 242 to provide additional mechanical support for the proximal portion of a lead inserted within first electrical connector 250 of first lead connection assembly 244. For example, the proximal portion of a lead extending out of electrical connector 250 may be prevented from bending in the direction of second lead connection assembly 246, e.g., due to engagement with the housing of second lead connection assembly 246 by virtue of the position of first lead connection assembly 244 relative to second lead connection assembly 246 on housing 248. In some examples, the housing of second lead connection assembly 246 may be shaped to guide the lead away from housing 248. In some examples, the housing of second lead connection assembly 246 may be configured such that a portion of a lead connected to first electrical connector 250 of first lead connection assembly 244 may be affixed, e.g., via a mechanical fastener, to the housing of second lead connection assembly 246 to provide additional mechanical support for the proximal portion of a lead connected to first electrical connector 250, as well as functioning to secure the proximal end of the lead within first electrical connector 250.

In each case, first and second lead connection assemblies 244, 246 are configured relative to one another on housing 248 such that one of the lead connection assemblies provides a support "ledge" for a lead connected in the electrical connector of the other lead connection assembly. Furthermore, the lead connection assembly configurations shown in FIGS. 14 and 15 may allow a clinician to make a single incision to access the leads connected to IMD 242, e.g., to expose the proximal portion of both leads in assemblies 244, 246 to dissect surrounding tissue.

The lead connection assemblies described herein are merely examples of the disclosure and the disclosure is not limited to such configurations. Instead, in some examples, any suitable electrical connectors known in the art may be utilized. In some examples, particular electrical connectors may be selected to define a therapy system having a first lead that is incompatible with a second electrical connector, as described herein. Furthermore, examples of the present disclosure may not be limited to therapy systems configured to deliver one or two different types of stimulation therapy to a patient. In some examples, an IMD may include two or more therapy modules configured to deliver different types of stimulation therapies to a patient. In such cases, a lead connection assembly may include two or more electrical connectors that correspond to each therapy module. Alternatively, an IMD may include multiple lead connection assemblies corresponding to different therapy modules within the IMD. In other example, an IMD may include a single therapy module configured to deliver stimulation therapy to a patient via two or more lead connection assemblies.

In general, configuration of the electrical connectors of lead connection assemblies described herein may be modified to be consistent with the type of lead being used to deliver electrical stimulation therapy to a patient from IMD and still be within the scope of the disclosure. For example, a number of electrical contacts of an electrical connector may correspond to the number of electrical contacts of a lead that is electrically connected to the electrical connector.

The techniques described in this disclosure, including those attributed to IMD 14, IMD 228 and programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 45 (FIG. 2) of IMD 14 or processor 220 of IMD 228 (FIG. 11), any one or more parts of the techniques described herein may be implemented by a processor of one of IMD 14, IMD 228, programmer 24 or another computing device, alone or in combination with IMD 14, IMD 228 or programmer 24.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described herein. These and other examples are within the scope of the following claims.

The invention claimed is:

1. An implantable medical system comprising:
a housing;
a first therapy module enclosed within the housing and configured to generate a first electrical stimulation therapy for delivery to a patient;
a second therapy module enclosed within the housing and configured to generate a second electrical stimulation therapy for delivery to the patient;
a first lead connection assembly including a first electrical connector electrically coupled to the first therapy module; and
a second lead connection assembly including a second electrical connector electrically coupled to the second therapy module,
wherein the first electrical connector defines a first opening and the second electrical connector defines a second opening, and
wherein the first opening faces a first direction and the second opening faces a second direction that is substantially orthogonal to the first direction.

2. The implantable medical system of claim 1, wherein the first and second lead connection assemblies are distributed around an outer perimeter of the housing.

3. The implantable medical system of claim 1, wherein the first lead connection assembly is located adjacent a first portion of the housing, and the second lead connection assembly is located adjacent a second portion of the housing that differs from the first portion.

4. The implantable medical system of claim 1, wherein the first electrical connector is configured to electrically couple a first lead to the first therapy module, and the second electrical connector is configured to electrically couple a second lead to the second therapy module.

5. The implantable medical system of claim 4, wherein the first and second electrical connectors comprise at least one of a different size, a different shape and a different electrical contact arrangement.

6. The implantable medical system of claim 1, further comprising a third lead connection assembly including a third electrical connector, the third electrical connector being electrically coupled to one of the first therapy module or the second therapy module.

7. The implantable medical system of 6, wherein the third electrical connector defines a third opening, wherein the first, second, and third openings face in different directions.

8. The implantable medical system of claim 1, wherein the first therapy module comprises a first therapy module configured to generate at least one of pacing, cardioversion and defibrillation therapy that is delivered to a heart of the patient.

9. The implantable medical system of claim 8, wherein the second therapy module comprises a second therapy module configured to generate second electrical stimulation that is delivered to a tissue site within the patient, the tissue site comprising at least one of a nonmyocardial tissue site and nonvascular cardiac tissue site.

10. The implantable medical system of claim 9, wherein the tissue site comprises at least one of an extravascular tissue site and a tissue site proximate a nerve.

11. The implantable medical system of claim 1, wherein the housing comprises a disk-shaped housing, and the first and second lead connection assemblies have different radial positions on the disk-shaped housing.

12. A method comprising:
delivering a first electrical stimulation therapy to a patient via a first lead electrically coupled to a first therapy module of an implantable medical device via a first lead connection assembly comprising a first electrical connector electrically coupled to the first therapy module; and
delivering a second electrical stimulation therapy to the patient via a second lead electrically coupled to a second therapy module of an implantable medical device via a second lead connection assembly comprising a second electrical connector electrically coupled to the second therapy module,
wherein the implantable medical device comprises a housing,
wherein the first electrical connector defines a first opening and the second electrical connector defines a second opening, and
wherein the first opening faces a first direction and the second opening faces a second direction that is substantially orthogonal to the first direction.

13. The method of claim 12, wherein the first and second lead connection assemblies are distributed around an outer perimeter of the housing.

14. The method of claim 12, wherein the first lead connection assembly is located adjacent a first portion of the housing, and the second lead connection assembly is located adjacent a second portion of the housing that differs from the first portion.

15. The method of claim 12, wherein the first electrical connector is configured to electrically couple a first lead to the first therapy module, and the second electrical connector is configured to electrically couple a second lead to the second therapy module.

16. The method of claim 15, wherein the first and second electrical connectors comprise at least one of a different size, a different shape and a different electrical contact arrangement.

17. The method of claim 12, further comprising a third lead connection assembly including a third electrical connector, the third electrical connector being electrically coupled to one of the first therapy module or the second therapy module.

18. The method of 17, wherein the third electrical connector defines a third opening, wherein the first, second, and third openings face in different directions.

19. The method of claim 12, wherein the first therapy module comprises a first therapy module configured to generate at least one of pacing, cardioversion and defibrillation therapy that is delivered to a heart of the patient.

20. The method of claim 19, wherein the second therapy module comprises a second therapy module configured to generate second electrical stimulation that is delivered to a tissue site within the patient, the tissue site comprising at least one of a nonmyocardial tissue site and nonvascular cardiac tissue site.

21. The method of claim 20, wherein the tissue site comprises at least one of an extravascular tissue site and a tissue site proximate a nerve.

22. The method of claim 12, wherein the housing comprises a disk-shaped housing, and the first and second lead connection assemblies have different radial positions on the disk-shaped housing.

23. An implantable medical system comprising:
a housing;
means for generating a first electrical stimulation for delivery to a patient;
means for generating a second electrical stimulation for delivery the patient separate from that of the means for generating first electrical stimulation;
means for electrically coupling a first implantable lead to the means for generating first electrical stimulation;
means for electrically coupling a second implantable lead to the means for generating second electrical stimulation separate from that of the means for electrically coupling the first implantable lead to the means for generating first electrical stimulation,
wherein the means for generating the first electrical stimulation and the second electrical stimulation are enclosed within the housing,
wherein the means for electrically coupling the first implantable lead to the means for generating first electrical stimulation comprises a first electrical connector electrically coupled to the means for generating the first electrical stimulation, and the means for electrically coupling the second implantable lead to the means for generating second electrical stimulation comprises a second electrical connector electrically coupled to the means for generating the second electrical stimulation,
wherein the first electrical connector defines a first opening and the second electrical connector defines a second opening, and
wherein the first opening faces a first direction and the second opening faces a second direction that is substantially orthogonal to the first direction.

24. The implantable medical system of claim 23, wherein the means for electrically coupling the first implantable lead to the means for generating first electrical stimulation comprises a first lead connection assembly including the first electrical connector, and the means for electrically coupling the second implantable lead to the means for generating second electrical stimulation comprises a second lead connection assembly including the second electrical connector.

25. The implantable medical system of claim 24, wherein the first and second lead connection assemblies are distributed around an outer perimeter of the housing.

26. An implantable medical system comprising:
a housing;
a first therapy module enclosed within the housing and configured to generate a first electrical stimulation therapy for delivery to a patient;
a second therapy module enclosed within the housing and configured to generate a second electrical stimulation therapy for delivery to the patient;
a first lead connection assembly including a first electrical connector electrically coupled to the first therapy module;
a second lead connection assembly including a second electrical connector electrically coupled to the second therapy module; and
a third lead connection assembly including a third electrical connector, the third electrical connector being electrically coupled to one of the first therapy module or the second therapy module,
wherein the first electrical connector defines a first opening, the second electrical connector defines a second opening, and the third electrical connector defines a third opening, and
wherein the first, second, and third openings each face in different directions.

27. The implantable medical system of claim 26, wherein the first and second lead connection assemblies are distributed around an outer perimeter of the housing.

28. The implantable medical system of claim 26, wherein the first lead connection assembly is located adjacent a first portion of the housing, and the second lead connection assembly is located adjacent a second portion of the housing that differs from the first portion.

29. The implantable medical system of claim 26, wherein the first electrical connector is configured to electrically couple a first lead to the first therapy module, and the second electrical connector is configured to electrically couple a second lead to the second therapy module.

30. The implantable medical system of claim 29, wherein the first and second electrical connectors comprise at least one of a different size, a different shape and a different electrical contact arrangement.

31. The implantable medical system of claim 26, wherein the first opening and the second opening face substantially opposite directions.

32. The implantable medical system of claim 26, wherein the first opening faces a first direction and the second opening faces a second direction that is substantially orthogonal to the first direction.

33. The implantable medical system of claim 26, wherein the first therapy module comprises a first therapy module configured to generate at least one of pacing, cardioversion and defibrillation therapy that is delivered to a heart of the patient.

34. The implantable medical system of claim 33, wherein the second therapy module comprises a second therapy module configured to generate second electrical stimulation that is delivered to a tissue site within the patient, the tissue site comprising at least one of a nonmyocardial tissue site and nonvascular cardiac tissue site.

35. The implantable medical system of claim 34, wherein the tissue site comprises at least one of an extravascular tissue site and a tissue site proximate a nerve.

36. The implantable medical system of claim 26, wherein the housing comprises a disk-shaped housing, and the first and second lead connection assemblies have different radial positions on the disk-shaped housing.

37. A method comprising:
delivering a first electrical stimulation therapy to a patient via a first lead electrically coupled to a first therapy module of an implantable medical device via a first lead connection assembly comprising a first electrical connector electrically coupled to the first therapy module;
delivering a second electrical stimulation therapy to the patient via a second lead electrically coupled to a second therapy module of the implantable medical device via a second lead connection assembly comprising a second electrical connector electrically coupled to the second therapy module, wherein the implantable medical device comprises a housing, wherein the implantable medical device further comprises a third lead connection assembly including a third electrical connector, the third electrical connector being electrically coupled to one of the first therapy module or the second therapy module, wherein the first electrical connector defines a first opening, the second electrical connector defines a second opening, and the third electrical connector defines a third opening, and wherein the first, second, and third openings each face in different directions.

38. The method of claim 37, wherein the first and second lead connection assemblies are distributed around an outer perimeter of the housing.

39. The method of claim 37, wherein the first lead connection assembly is located adjacent a first portion of the housing, and the second lead connection assembly is located adjacent a second portion of the housing that differs from the first portion.

40. The method of claim 37, wherein the first electrical connector is configured to electrically couple a first lead to the first therapy module, and the second electrical connector is configured to electrically couple a second lead to the second therapy module.

41. The method of claim 40, wherein the first and second electrical connectors comprise at least one of a different size, a different shape and a different electrical contact arrangement.

42. The method of claim 37, wherein the first opening and the second opening face substantially opposite directions.

43. The method of claim 37, wherein the first opening faces a first direction and the second opening faces a second direction that is substantially orthogonal to the first direction.

44. The method of claim 37, wherein the first therapy module comprises a first therapy module configured to generate at least one of pacing, cardioversion and defibrillation therapy that is delivered to a heart of the patient.

45. The method of claim 44, wherein the second therapy module comprises a second therapy module configured to generate second electrical stimulation that is delivered to a tissue site within the patient, the tissue site comprising at least one of a nonmyocardial tissue site and nonvascular cardiac tissue site.

46. The method of claim 37, wherein the housing comprises a disk-shaped housing, and the first and second lead connection assemblies have different radial positions on the disk-shaped housing.

47. An implantable medical system comprising:
a housing;
means for generating a first electrical stimulation for delivery to a patient;

means for generating a second electrical stimulation for delivery the patient separate from that of the means for generating the first electrical stimulation;

means for electrically coupling a first implantable lead to the means for generating the first electrical stimulation, the means for electrically coupling the first implantable lead to the means for generating the first electrical stimulation comprising a first electrical connector electrically coupled to the means for generating the first electrical stimulation;

means for electrically coupling a second implantable lead to the means for generating the second electrical stimulation separate from that of the means for electrically coupling the first implantable lead to the means for generating first electrical stimulation, the means for electrically coupling the second implantable lead to the means for generating second electrical stimulation comprising a second electrical connector electrically coupled to the means for generating the second electrical stimulation; and means for electrically coupling a third implantable lead to one of the means for generating the first electrical stimulation or the means for generating the second electrical stimulation, the means for electrically coupling the third implantable lead to one of the means for generating the first electrical stimulation or the means for generating the second electrical stimulation comprising a third electrical connector electrically coupled to the one of the means for generating the first electrical stimulation or the means for generating the second electrical stimulation, wherein the means for generating the first electrical stimulation and the second electrical stimulation are enclosed within the housing, wherein the first electrical connector defines a first opening, the second electrical connector defines a second opening, and the third electrical connector defines a third opening, and wherein the first, second, and third openings each face in different directions.

48. The implantable medical system of claim 47, wherein the means for electrically coupling the first implantable lead to the means for generating first electrical stimulation comprises a first lead connection assembly including the first electrical connector, and the means for electrically coupling the second implantable lead to the means for generating second electrical stimulation comprises a second lead connection assembly including the second electrical connector.

49. The implantable medical system of claim 48, wherein the first and second lead connection assemblies are distributed around an outer perimeter of the housing.

* * * * *